US010080793B2

(12) United States Patent
van't Oever et al.

(10) Patent No.: US 10,080,793 B2
(45) Date of Patent: Sep. 25, 2018

(54) METHODS FOR THE PREVENTION OF AGGREGATION OF VIRAL COMPONENTS

(71) Applicant: DE STAAT DER NEDERLANDEN, VERT. DOOR DE MINISTER VAN VWS, MINISTERIE VAN VOLKSGEZONDHEID, WELZIJN EN SPORT, The Hauge (NL)

(72) Inventors: Arend Gesinus van't Oever, Zwolle (NL); Wilfridus Adrianus Maria Bakker, Almere (NL); Yvonne Elisabeth Thomassen, Wageningen (NL)

(73) Assignee: De Staat der Nederlanden, vert, door de minister van VWS, Ministerie van Volksgezonheid, Welzijn en Sport, The Hague (NL)

( * ) Notice: Subject to any disclaimer, the term of this patent is extended or adjusted under 35 U.S.C. 154(b) by 46 days.

(21) Appl. No.: 14/898,654

(22) PCT Filed: Jun. 17, 2014

(86) PCT No.: PCT/NL2014/050395

§ 371 (c)(1),
(2) Date: Dec. 15, 2015

(87) PCT Pub. No.: WO2014/204303

PCT Pub. Date: Dec. 24, 2014

(65) Prior Publication Data

US 2016/0184423 A1 Jun. 30, 2016

(30) Foreign Application Priority Data

Jun. 17, 2013 (EP) .................................... 13172263

(51) Int. Cl.

| | |
|---|---|
| ***A61K 39/13*** | (2006.01) |
| ***C12N 7/00*** | (2006.01) |
| ***A61K 39/12*** | (2006.01) |
| ***A61K 39/145*** | (2006.01) |
| *A61K 39/00* | (2006.01) |

(52) U.S. Cl.

CPC .............. *A61K 39/13* (2013.01); *A61K 39/12* (2013.01); *A61K 39/145* (2013.01); *C12N 7/00* (2013.01); *A61K 2039/5252* (2013.01); *A61K 2039/545* (2013.01); *C12N 2760/16051* (2013.01); *C12N 2760/16134* (2013.01); *C12N 2760/18051* (2013.01); *C12N 2770/32051* (2013.01); *C12N 2770/32351* (2013.01); *C12N 2770/32634* (2013.01); *C12N 2770/32651* (2013.01); *C12N 2770/32663* (2013.01)

(58) Field of Classification Search

None

See application file for complete search history.

(56) References Cited

U.S. PATENT DOCUMENTS

| | | | | |
|---|---|---|---|---|
| 5,618,539 | A | 4/1997 | Dorval et al. | |
| 2006/0035364 | A1 | 2/2006 | Wright et al. | |
| 2008/0193478 | A1 * | 8/2008 | Jain | A61K 39/13 424/202.1 |
| 2011/0027317 | A1 | 2/2011 | Lewis | |
| 2012/0273424 | A1 | 11/2012 | Coffey et al. | |

FOREIGN PATENT DOCUMENTS

WO WO-2009/035707 A1 3/2009

OTHER PUBLICATIONS

Baynes et al., Biochemistry, 2005, 44:4919-4925.*

Urakawa et al., Journal of General Virology, 1989, 70:1453-1463.*

Aylward et al., "The global polio eradication initiative: Lessons learned and prospects for success", Vaccine 29S, 2001, pp. D80-D85.

Bakker et al., "Inactivated polio vaccine development for technology transfer using attenuated Sabin poliovirus strains to shift from Salk-IPV to Sabin-IPV", Vaccine 29, 2001, pp. 7188-7196.

Chumakov et al., "Vaccination against polio should not be stopped", Nature Reviews Microbiology, Dec. 2007, vol. 5, pp. 952-958.

Cromwell et al., "Protein aggregation and bioprocessing", The AAPS Journal, 2006, vol. 8, No. 3, Article 66, pp. E572-579.

Duchene et al., "Production of poliovirus vaccines: past, present, and future", Viral Immunology,1990, vol. 3, No. 4, pp. 243-272.

Gu et al., "Inhibition of aggregation by media selection, sample loading and elution in size exclusion chromatographic refolding of denatured bovine carbonic anhydrase B", J. Biochem. Biophys. Methods, 2003, vol. 56, pp. 165-175.

Hamidi et al., "Innovative IPV form attenuated Sabin poliovirus or newly designed alternative seed strains", Pharmaceutical Patent Analyst, 2012, vol. 1, No. 5, pp. 589-599.

Heinsbroek et al., "The global introductions of inactivated polio vaccine can circumvent the oral polio vaccine paradox", Vaccine, 2010, vol. 28, pp. 3778-3783.

Heymann et al., "A global call for new polio vaccines", Nature, Apr. 7, 2005, vol. 434, pp. 699-700.

Heymann et al., "A vision of a world without polio: The OPV cessation strategy", Biologicals, 2006, vol. 34, pp. 75-79.

Kew et al., "Vaccine-derived polioviruses and the endgame strategy for global polio eradication", Annu. Rev. Microbiol., 2005, vol. 59, pp. 587-635.

Koonin et al., "The ancient virus world and evolution of cells", Biology Direct, 2006, vol. 1, No. 29, pp. 1-27.

Lee et al., "Attenuated vaccines can recombine to form virulent field viruses", Science, Jul. 13, 2012, vol. 337, p. 188.

Nathanson et al., "From emergence to eradication: The epidemiology of poliomyelitis deconstructed", American Journal of Epidemiology, Oct. 26, 2010, vol. 172, No. 11, pp. 1213-1229.

Robinson, "Viral attenuation by design", Nature Biotechnology, Sep. 2008,vol. 26, No. 9, pp. 1000-1001.

(Continued)

*Primary Examiner* — Stacy Brown Chen

(74) *Attorney, Agent, or Firm* — Gilberto M. Villacorta; Sunit Talapatra; Foley & Lardner LLP

(57) ABSTRACT

The present invention relates to a method for prevention and/or reduction of aggregation of viral components.

14 Claims, 12 Drawing Sheets

(56) References Cited

OTHER PUBLICATIONS

Taylor et al., "Toxic proteins in neurodegenerative disease", Science, Jun. 14, 2002, vol. 296, pp. 1991-1995.

Thompson et al., "Current polio global eradication and control policy options: perspectives from modeling and prerequisites for oral poliovirus vaccine cessation", Expert Reviews Vaccines, 2012, vol. 11, No. 4, pp. 449-459.

Wang, "Protein aggregation and its inhibition in biopharmaceutics", International Journal of Pharmaceautics, 2005, vol. 289, pp. 1-30.

Baynes et al., "Role of Arginine in the stabilization of proteins against aggregation." Biochemistry, Mar. 2005, vol. 44, No. 12, pp. 4919-4925.

Brautigam et al., "Formation of Poliovirus-like particles by recombinant baculoviruses expressing the individual VP0, VP3, and VP1 proteins by comparison to particles derived from the expressed poliovirus polyprotein." Virology, Feb. 1993, vol. 192, No. 2, pp. 512-524.

International Search Report and Written Opinion of the International Searching Authority issued in International Patent Application No. PCT/NL2014/050395, dated Aug. 25, 2015.

* cited by examiner

METHODS FOR THE PREVENTION OF AGGREGATION OF VIRAL COMPONENTS

CROSS-REFERENCE TO RELATED APPLICATIONS

This application is the National Phase of International Patent Application No. PCT/NL2014/050395, filed Jun. 17, 2014, published on Dec. 24, 2014 as WO 2014/204303 A2, which claims priority to European Patent Application No. 13172263.9, filed Jun. 17, 2013. The contents of these applications are herein incorporated by reference in their entirety.

FIELD OF THE INVENTION

The present invention relates to a method for the prevention and/or reduction of aggregation of viral components. The invention therefore relates to the field of production and formulation of biopharmaceuticals and to the field of vaccinology.

BACKGROUND OF THE INVENTION

Aggregation is a well known problem in the production of (bio-) pharmaceuticals, especially proteins such as monoclonal antibodies and viruses. More background on protein aggregation may be found in the following review (Wei Wang, 2005). Aggregation can be associated with high production/manufacturing losses, instability, reduced shelf life, adverse effects upon administration, different immunogenic reactions, and up to disease formation itself (like e.g., Alzheimer Parkinson (Taylor et al. 2002), prion encephalopathy and Huntington's). Aggregation may be prevented by careful selection of buffers or media applied in the production process (Gu et al., 2003, Cromwell et al. 2006). Addition of compounds like urea or guanidinium salts has been known to solubilize proteins. However, these agents also affect protein structure and efficacy. Suppressing or preventing aggregation is not always successful and compromises have to be made which may lead to (relatively) high product losses during manufacturing, storage or loss of efficacy over time.

During the production of viral components such as e.g. Sabin based inactivated poliovirus, unwanted aggregation is also known to occur, which may give rise to large variations in purification product recovery (yield) in viral (components) manufacturing. There is thus a need for an improved method for the production of viral components.

Viruses are infectious agents that can only replicate inside living cells, depending on the virus they may infect different types of organisms such as animals, plants, bacteria and archaea (Koonin E V et al. 2006). The virus consists of two or three distinct parts, the genetic material and a viral protein coat, sometimes supplemented by a lipid-bilayer membrane or envelope. The viral coat is made up out of multiple proteins, which form a highly complex quaternary structure in a helical, isocahedral or even more complex structure. More background on viruses may be found in the following reference (Fields Virology, 2007).

In our study we focused on poliovirus and influenza as a model for non-enveloped and enveloped viruses, respectively. Poliovirus is commonly used as a non-specific model virus for non-enveloped RNA viruses in viral removal validation studies as representative of Picornaviruses in general (technical note Millipore: AN1650EN00, www.bioreliance.com/library/?id=90, http://www.criver.com/files/pdfs/bps/bp_r_viral_tse-clearance_studies.aspx). Furthermore poliovirus is a well studied virus on which a huge body of scientific literature is available making it a suitable candidate. As a representative of enveloped viruses different strains of influenza were used. Influenza is a virus which is causing a great deal of concern each year due to it's variability (antigenic drift). Influenza is studied worldwide and due to the disease burden a likely target for any vaccine improvement. The high variability make influenza virus a suitable representative to quickly test this method for reducing and preventing of aggregation against many variations, showing the wide range in which this technique may be used.

Poliomyelitis, also referred to as polio or infantile paralysis, is an infectious viral disease caused by three related virus serotypes: poliovirus type 1, 2 and 3. Polioviruses belong to the genus Enteroviruses in the Picornaviridae family. In humans, polioviruses are mainly acquired by fecal-oral or oral-oral transmission. After infection, poliovirus proliferates in the gastrointestinal tract, and from there it can enter the central nervous system. Such an infection may cause paralysis. Polio cannot be cured. However, it can be prevented by vaccination. Currently, there are two safe and effective polio vaccines available in the market: Oral Polio Vaccine (OPV), and Inactivated Polio Vaccine (IPV). OPV is based on life-attenuated strains of the poliovirus (the so-called Sabin strains, after Albert Sabin, who first developed OPV), this vaccine is administered via the oral route. In contrast, IPV, is based on using purified wild-type poliovirus strains, which are chemically killed and is administered intramuscular by injection. IPV was first developed by Jonas Salk [there are several reviews available on polio and polio vaccines: Koch and Koch, 1985; Duchene et al., 1990; Kew et al. 2005; Heinsbroek and Ruitenberg, 2010].

Both available polio vaccines (OPV and IPV) provide high levels of protection from paralytic poliomyelitis. OPV has thus far been the vaccine of choice for the global polio eradication as it has several advantages: easy to administer and less expensive. However, in some cases OPV may cause vaccine associated paralytic poliomyelitis (VAPP) or may lead to vaccine derived poliovirus (VDPV), and should be preferably discontinued as soon as eradication is successful [Kew et al., 2005; Heymann et al., 2005 & 2006; Chumakov et al., 2007; Nathanson & Kew, 2010; Aylward and Tangermann, 2011]. It is also not excluded that OPV might revert back to the wild type variant (Lee et al 2012). Therefore, the need for new, safe and effective polio vaccines is increasing. The pathway to a global post-eradication polio vaccination policy depends on, amongst others, the availability and price of IPV [Heinsbroek and Ruitenberg, 2010; Thompson and Tebbens, 2012].

To discontinue the use of OPV after polio eradication, and to reduce the cost of IPV per dose, different approaches are being followed. Amongst others, these approaches include: a) IPV based on the attenuated Sabin poliovirus strains (Sabin-IPV) [Bakker et al., 2011; Hamidi & Bakker, 2012]; b) IPV based on newly designed alternative poliovirus seed strains [Chumakov et al., 2008; Robinson H L 2008; Hamidi & Bakker, 2012]; c) IPV produced from alternative mammalian cells that efficiently support poliovirus replication [Hamidi & Bakker, 2012; Sanders et al., 2012; Crucell, U.S. Pat. No. 0,027,317, 2011]. In all such developments, opportunities in cost price reduction can be realized by implementation of known methods in up-stream and down-stream process optimization (e.g. more efficient use of bioreactor capacity), and overall modernization (e.g. using animal-component-free cell and virus culture media, disposable filters and alike).

Currently, IPV is most commonly based on using three wild-type virulent strains, Mahoney (type 1 poliovirus), MEF-1 (type 2 poliovirus), and Saukett (type 3 poliovirus). The polioviruses are grown separately in mammalian cell culture. Subsequently, after several purification steps, the poliovirus is inactivated using formalin (formaldehyde) whereafter they can be mixed to the final desired formulation and filled.

Influenza virus causes an acute respiratory infection, with considerable morbidity and mortality. Prevalence is highest in school-aged children. Small children, elderly and those with conditions such as lung and heart disease, diabetes or severe asthma are at risk for severe influenza. Clinically, influenza comprises acute febrile illness with myalgia, headache and cough.

Although the disease influenza has been known for centuries, the causative agent was long unknown. The first human influenza virus was isolated in 1933.

The virus could be propagated on embryonated eggs (still a common practice, later complemented with the ability to grow the virus on cell cultures), which greatly facilitated the ability to study the virus.

The influenza virus is an RNA viruses of the family Orthomyxoviridae and is composed of a lipid envelope around eight segments of RNA. On the envelope two major proteins (antigens) are present: the neuraminidase (NA/N) and the haemagglutinin (HA/H). Haemagglutinin is the protein that attaches the virus to cells of the respiratory epithelium and subsequently fuses the viral membrane with the membrane of the epithelial cell, to allow the virus entry. The neuraminidase is a viral enzyme that facilitates the release of newly produced viral particles from infected cells.

Besides man, influenza viruses can infect a wide range of animal species, the most relevant for humans being birds and pigs, because the viruses from these species can generally also infect humans. A marked feature of influenza viruses is variability. Variation is driven by immune selection, meaning that the virus will constantly try to escape host immunity. It can do so by gradual mutation of its antigens known as antigenic drift or by swapping entire RNA segments coding for antigens with related strains, known as antigenic shift. Immune selection pertains to antibody responses against the surface antigens, and to a lesser extent to T-cell responses, which are mainly directed against the internal proteins.

Due to antigenic drift, new vaccines against seasonal influenza need to be produced each year, containing the antigens that are expressed on the circulating viral strains in the respective season. Antigenic shift, or a series of antigenic drift mutations, may cause a pandemic. Protection against a pandemic outbreak necessitates the usage of newly developed potent vaccines containing the antigens expressed by the pandemic virus.

As explained herein, the inventors identified an improved method for the production of viral components and for an improved composition comprising such viral components, wherein aggregation is prevented or reduced.

SUMMARY OF THE INVENTION

In a first aspect the invention relates to a method for producing a composition comprising Enteroviral particles, wherein the method comprises the steps of: a) producing a medium containing the Enteroviral particles; b) purification of the Enteroviral particles from the medium, whereby during at least a part of the purification a basic amino acid or a derivative thereof is present at a concentration sufficient to prevent or reduce aggregation of the Enteroviral particles; and, optionally, at least one of: c) inactivation of the Enteroviral particles; and, d) formulation of the Enteroviral particles, wherein the basic amino acid or derivative thereof is selected from the group consisting of: arginine, lysine, histidine, arginine-HCl, lysine-HCl, histidine-HCl, agmatine, L-arginine ethyl ester dihydrochloride, tranexamic acid, N-ε-formyl-L-lysine, DL-5-hydroxylysine hydrochloride, L-lysine methyl ester dihydrochloride, 3-methyl-L-histidine, α-methyl-DL-histidine dihydrochloride, salts thereof and combinations thereof.

Preferably in the method, the basic amino acid or derivative thereof is present at a concentration sufficient to prevent or reduce aggregation of the Enteroviral particles during at least a part of step c), and wherein, optionally, also during step d) the basic amino acid or derivative thereof is present at a concentration sufficient to prevent or reduce aggregation of the Enteroviral particles to formulate a pharmaceutical composition comprising the Enteroviral particles and optionally a concentration of the basic amino acid or derivative thereof sufficient to prevent or reduce aggregation of the Enteroviral particles.

More preferably, in the method preferably, the concentration of the basic amino acid or derivative thereof that is sufficient to prevent or reduce aggregation of the Enteroviral particles is maintained throughout the entire duration of at least one of steps b), c) and d).

In the method according to the invention, the concentration of the basic amino acid or derivative thereof preferably is a concentration of at least 0.01 mM, preferably a concentration in the range of 0.01-1000 mM.

In the method according to the invention, the Enteroviral particles preferably are of an *Enterovirus* selected from the group consisting of polioviruses, Coxsackie A viruses, Coxsackie B viruses, Echoviruses and Enteroviruses 68, 69, 70, 71 and 73. More preferably, the Enteroviral particles comprise polioviruses of the serotypes 1, 2 and 3. In one embodiment, the Enteroviral particles preferably are virus-like particles of an *Enterovirus* .

In the method according to the invention the composition comprising Enteroviral particles preferably is a vaccine. More preferably, the vaccine is an Inactivated Polio Vaccine (IPV).

The invention further pertains to the use of a basic amino acid or derivative thereof selected from the group consisting of: arginine, lysine, histidine, arginine-HCl, lysine-HCl, histidine-HCl, agmatine, L-arginine ethyl ester dihydrochloride, tranexamic acid, N-ε-formyl-L-lysine, DL-5-hydroxylysine hydrochloride, L-lysine methyl ester dihydrochloride, 3-methyl-L-histidine, α-methyl-DL-histidine dihydrochloride, salts thereof and combinations thereof, for preventing or reducing aggregation of Enteroviral particles, wherein preferably, Enteroviral particles are of an *Enterovirus* selected from the group consisting of polioviruses, Coxsackie A viruses, Coxsackie B viruses, Echoviruses, Rhinoviruses and Enteroviruses 68, 69, 70, 71 and 73, more preferably, the Enteroviral particles are polioviruses of at least one of the serotypes 1, 2 and 3, most preferably, the Enteroviral particles are an Inactivated Polio Vaccine (IPV).

In another aspect the invention relates to a composition comprising viral particles of a virus that belongs to the Paramyxoviridae or to the Orthomyxoviridae, and a basic amino acid or derivative thereof selected from the group consisting of: arginine, lysine, histidine, arginine-HCl, lysine-HCl, histidine-HCl, agmatine, L-arginine ethyl ester dihydrochloride, tranexamic acid, N-ε-formyl-L-lysine, DL-5-hydroxylysine hydrochloride, L-lysine methyl ester dihydrochloride, 3-methyl-L-histidine, α-methyl-DL-histidine dihydrochloride, salts thereof and combinations thereof, wherein: a) the total concentration of the basic amino acids or derivatives in the composition is higher than the total concentration of the basic amino acid or derivatives thereof as present in a culture medium; b) the composition does not comprise a buffer, and preferably does not comprise phenol red; and/or, c) the composition essentially consist of the viral particles, the basic amino acid or a derivative thereof in a total concentration of at least 0.01 mM and, optionally water or other liquid carrier. Preferably in the composition, the formation of viral aggregates in said composition is reduced compared to the formation of viral aggregates in a corresponding composition not comprising said basic amino acid or derivative thereof.

In yet another aspect the invention relates to a composition as defined above, for use as a medicament.

DESCRIPTION OF THE INVENTION

We have surprisingly found that basic amino acids (such as e.g. arginine), and several derivatives thereof, can be used for the prevention of aggregate formation, and for the solubilisation (dissolution/break-up) of already formed aggregates, both during processing of different viruses (enveloped (i.e. influenza) and non-enveloped (i.e. poliovirus)) in vaccine manufacturing, as well as during storage of (intermediate) viral products. These viruses were derived from different culture systems (influenza by embryonated eggs and poliovirus by cell culture). As a result, significantly higher virus product recoveries have been achieved and/or better removal of contaminants while maintaining a biological active product. These higher virus yields, which provides significant economic advantages over known virus purification methods, were not foreseen.

Prevention of aggregation using basic amino acids has been shown previously for monoclonal antibodies (MAbs) (Arakawa T, et al, 2004; US2012264918) and proteins (Baynes B M, 2004 and 2005). However it was not demonstrated for highly complex quaternary protein structures like viruses. In the case of *Clostridium* Toxoid (US 2011/0045025), arginine even facilitated aggregation.

Moreover, basic amino acid, such as arginine has further been shown to have virucidal activities (Yamasaki H, et al, 2008; Utsunimoya H, et al, 2009; Arakawa T, et al, 2009) making them unlikely agents for use during processing of viruses and viral components.

Ways of suppressing aggregation of normal proteins using basic amino acids have already been identified. In the present invention, we discovered that aggregation could be suppressed, reduced and/or prevented for highly complex structures made up out of several different proteins “blocks” (poly protein/multi subunit structures) which form a stable quaternary structure (as is the case for viral vaccines or biological complexes). The skilled person understands that some proteins alone form a tertiary structure which in some cases may be stabilized by a basic amino acid. However, viruses consist of multiple of these (different) tertiary structures together and bond/assemble to form a (temporary)/stable product (quaternary structure) with a helical, isocahedral or even a more complex structure. One of the viruses tested in the present invention has such a kind of complex structure since it comprises of a membrane envelop. Viruses differ from normal complex (biological) quarternary protein structures in the sense that they can replicate and multiply/reproduce themselves by using host cells and can evolve by natural selection (Holes E C 2007; Taylor D J, et al 2013). Furthermore some viruses have been shown to have the ability to form specialized structures for transporting genomic material into host cells (Sun L, et al 2014) or be parasitized upon by other viruses, so-called, virophages (Pearson H, 2008; and Desnues, C, et al 2010).

The entry of both enveloped and non-enveloped viruses into a cell requires interactions between cell receptors and the viral coat or envelope. They are specific for certain hosts cells like a key to a lock. This viral quaternary structure needs to be maintained in the correct conformation/structure (partly forms the viral coat) since its primary function is to protect (e.g. from heat, pH, UV, etc.) the genome in transit between cells and to bind to susceptible host cells, either internally within an embodiment or from the external environment into a completely new individual/host embodiment.

In view of the complexity, workings and intricacy of the structure of the viral components, the skilled person could not have foreseen that the use of a basic amino acid could prevent or reduce aggregation while the virus structure remains intact and the infectivity, specificity and immunogenicity are maintained.

Accordingly, in a first aspect, the invention relates to a method for the prevention and/or reduction of the aggregation of viral components comprising the use of a basic amino acid a derivative thereof or a mixture thereof. The method for preventing and/or reducing aggregation of viral components is preferably applied in or part of a method for producing a composition comprising viral components.

Basic Amino Acid or Derivative Thereof

A basic amino acid can be any D- or L-amino acid that is pharmaceutically acceptable. A basic amino acid can be in the form of an muriate (e.g. bound to one or more hydrochloric salts) or another coupled chemical form. Such amino acids include the 3 standard ‘proteinogenic’ or ‘natural’ amino acids: histidine, arginine, lysine as well as a derivative thereof. histidine, arginine and/or lysine may be either optical D- or L-isomers or mixtures thereof, although preferably the amino acid(s) are L-isomers.

A derivate of a basic amino acid may be any derivate form thereof that could be synthesized by a skilled person: see for example:

http://www.sigmaaldrich.com/chemistry/chemistryproducts.html?TablePage=162 5523 or Sigma Aldrich’s “Amino Acid Derivatives” product catalogue or any other commercial source.

A derivative of a basic amino acid may be a chiral or isomeric form of histidine, arginine or lysine. A derivative of a basic amino acid may be a metabolic product of histidine, arginine or lysine. Preferred derivates of lysine are selected from: tranexamic acid, N-ε-formyl-L-lysine and mono or dihydrochloride salts of lysine such as DL-5-Hydroxylysine hydrochloride and L-lysine methyl ester dihydrochloride. Preferred derivates of arginine are selected from: N-α-acetyl L-arginine, agmatine, agmatine sulphate salt and mono or dihydrochloride salts of arginine such as L-arginine ethyl ester dihydrochloride. Preferred derivates of histidine are selected from: 3-methyl-L-histidine and mono or dihydrochloride salts of histidine such as α-methyl-DL-histidine dihydrochloride.

In a preferred embodiment, the basic amino acid or a derivative thereof is selected from the group consisting of: L-arginine, D-arginine, L-lysine, L-histidine, chiral/isomeric/racemate forms of arginine, lysine, histidine, arginine-HCl, lysine-HCl, histidine-HCl, metabolic product of arginine, lysine, histidine, N-α-acetyl L-arginine, agmatine, agmatine sulphate salt, L-arginine ethyl ester dihydrochloride, tranexamic acid, N-ε-formyl-L-lysine, monohydrochloride salt of lysine, monohydrochloride salt of histidine, monohydrochloride salt of arginine, dihydrochloride salt of lysine, dihydrochloride salt of histidine, dihydrochloride salt of arginine, DL-5-hydroxylysine hydrochloride, L-lysine methyl ester dihydrochloride, 3-methyl-L-histidine and α-methyl-DL-histidine dihydrochloride, arginine-glutamate, arginine-acetate, arginine-aspartate, arginine-sulfate, lysine-glutamate, lysine-acetate, histidine-acetate, butyroyl-L-arginine, Nα-cocoyl-L-arginine ethyl ester, N-[3-alkyl (12,14)oxy-2-hydroxypropyl]-L-arginine hydrochloride, L-arginine cocoate. It is also encompassed that a basic amino acid or a derivative thereof may be combined to a salt form like arginine-glutamic acid, arginine-acetate acid, arginine-aspartate acid etc.

A basic amino acid or a derivative thereof may be added to a composition or solution comprising viral components and aggregates thereof to obtain a final concentration in the range of 0.01-1000 mM or 0.015-1000 mM, or at least 0.01, 0.015, 0.05, 0.10, 0.15, 0.20, 0.25, 0.30, 0.35, 0.40, 0.45, 0.5, 1, 5, 10, 15, 20, 25, 30, 35, 40, 45, 50, 60, 70, 80, 81, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 550, 600, 650, 700, 750, 800, 850, 900, 950, or 1000 mM and/or less than 1000 mM, 950, 900, 850, 800, 750, 700, 650, 600, 550, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 45, 40, 35, 30, 25, 20, 15, 10, 5, 1, 0.50, 0.45, 0.40, 0.35, 0.30, 0.25, 0.20, 0.15, 0.1, 0.05, 0.015 or 0.01 mM. If more than one distinct basic amino acid or derivative thereof is present in said composition or solution as later explained herein, the concentration identified above refers to the total concentration of basic amino acid or derivatives thereof. If only one basic amino acid or one derivative thereof is being used, the total concentration of basic amino acid or derivative thereof is synonymous with the concentration of said amino acid. It is understood that a basic amino acid or a derivative thereof can be added as an additive (also referred to as excipient, cosolvent or cosolute), as a solid (to be dissolved in the mixture), as an (concentrated) aqueous solution in water or buffer or exchanged against water or buffer containing said the basic amino acid via e.g. diafiltration, to a composition or solution comprising viral components and aggregates thereof.

Depending on the identity of the virus, the skilled person may adapt the concentration to reach the effect desired on the prevention or reduction of aggregation. For example for poliovirus, the concentration of a basic amino acid or derivate thereof is preferably not more than 100 mM or not more than 150 mM.

A preferred basic amino acid is arginine, more preferably L-arginine. A preferred concentration of L-arginine in said composition or solution comprising the viral components and aggregates thereof is ranged from 0.01-1000 mM, 0.015-1000 mM, 0.05-1000 mM, 0.1-1000 mM, 0.5-1000 mM, 0.8-1000 mM, 1-1000 mM, 0.1-900 mM, 0.8-900 mM, 1-900 mM, 0.1-800 mM, 0.8-800 mM, 0.1-700 mM, 0.5-700 mM, 1-600 mM, 5-500 mM, 10-400 mM, 15-300 mM, 20-200 mM, 25-200 mM, 30-200 mM, 35-200 mM, 40-200 mM, 45-200 mM, 50-300 mM, or 70-250 mM. Good results were obtained with 150 mM in the case of poliovirus and 350 mM in the case of influenza virus.

A preferred derivate or product from of arginine is agmatine. A preferred concentration of agmatine in said composition or solution comprising the viral components and aggregates thereof is ranged from 0.01-1000 mM, 0.015-1000 mM, 0.05-1000 mM, 0.1-1000 mM, 0.5-1000 mM, 0.8-1000 mM, 1-1000 mM, 0.1-900 mM, 0.8-900 mM, 1-900 mM, 0.1-800 mM, 0.8-800 mM, 0.1-700 mM, 0.5-700 mM, 1-600 mM, 5-500 mM, 10-400 mM, 15-300 mM, 20-200 mM, 25-200 mM, 30-200 mM, 35-200 mM, 40-200 mM, 45-200 mM, 50-300 mM or 70-250 mM. Good results were obtained with 100 mM and with 25 mM.

Another preferred basic amino acid is lysine, more preferably L-lysine. A preferred concentration of lysine in said composition or solution comprising the viral components and aggregates thereof is ranged from 0.01-1000 mM, 0.015-1000 mM, 0.05-1000 mM, 0.1-1000 mM, 0.5-1000 mM, 0.8-1000 mM, 1-1000 mM, 0.1-900 mM, 0.8-900 mM, 1-900 mM, 0.1-800 mM, 0.8-800 mM, 0.1-700 mM, 0.5-700 mM, 1-600 mM, 5-500 mM, 10-400 mM, 15-300 mM, 20-200 mM, 25-200 mM, 30-200 mM, 35-200 mM, 40-200 mM, 45-200 mM, 50-300 mM or 100-250 mM. Good results were obtained with 150 mM and with 75 mM.

The solution comprising a basic amino acid or a derivative thereof preferably has a neutral pH, e.g. a pH in the range of 6.0-8.0, or 6.5-7.5 or a pH of about 7.0. More preferably, the pH of the solution is below the pI of the basic amino acid that is used. This solution preferably comprises a buffer to maintain the pH at the indicated values. In principle any pharmaceutically acceptable buffer, which preferably has effective buffering capacity in the range of pH values as indicated, can be used in the solution. The buffer is preferably present in a concentration in the range of 0.5-100 mM, more preferably in the range of 1-75 mM and most preferably in the range of 2-40 mM, such as 20 or 40 mM.

Suitable buffers for use in the solution include, but not limited to, McIlvaine buffer (a mixture of 0.1M citric acid and 0.2M disodium phosphate), a citrate buffer, a phosphate buffer, a HEPES buffer, a PIPES buffer and a histidine buffer.

More preferably, each of the basic amino acid or derivates used herein is preferably buffered at pH 7. More preferably the buffer is a phosphate buffer at a concentration of 20 or 40 mM.

However, it is also encompassed within the context of the invention that no buffer is needed or no buffer is present. In this case, the composition or solution comprises or consists of the viral component and a basic amino acid or a derivative thereof as defined herein and no further buffer. Preferably said composition or solution consists of the viral component and a basic amino acid as defined herein.

It is encompassed within the context of the invention that more than one basic amino acids and/or more than one derivatives thereof are being used in a method of the invention for the prevention and/or reduction of the aggregation of viral components. A preferred combination of basic amino acid is a combination comprising arginine, lysine and histidine. It is also encompassed to use a given basic amino acid or derivative thereof in a given step of the process of the invention (i.e. an up-stream processing, a down-stream processing steps, an inactivation step and/or a formulation step) and to use a distinct basic amino acid or derivative thereof in another step of this same process. For example agmatine may be added to concentrated material, while arginine can be used during a downstream purification process step, e.g. during chromatographic step.

The basic amino acid can be added or be present during any step of the process, and it can but not need be present during all steps of the process. The basic amino acid can easily be removed or exchanged, when desired, by means of filtration, chromatography or dialysis (see Example 6).

Viral Components

A "viral component" is herein understood to refer to a biological agent, which is physiologically active or activates a physiological response when applied to a mammal, especially when applied to a human, preferably in a pharmaceutically acceptable form. A viral component may be produced by or obtainable from a host organism, such as animal, plant, bacteria or fungi. A viral component can be a protein-based agent, i.e. an agent comprising proteinaceous material such as proteins, polypeptides and peptides. A viral component may further comprise or consist of nucleic acid, e.g. DNA, RNA or a nucleic acid analogue. A viral component may further compromise membrane lipid(s) e.g. OMV's, liposomes, virosomes.

A preferred viral component comprises or consists of a virus or a virion, preferably a virus that infects mammals, preferably a virus that infects humans. The virus can be an enveloped virus but preferably is a non-enveloped virus. It is understood herein the term 'virus' or "viral component" as used herein include wild type viruses as they occur in nature (e.g. natural isolates), as well as 'man-made' attenuated, mutant, chimeric, pseudo- and defective viruses. The term 'virus' or "viral component" also includes recombinant viruses, i.e. viruses constructed using recombinant DNA technology, such as defective viruses, e.g. lacking (parts of) one, more or all viral genes and gene therapy vectors wherein part of the viral genome is replaced with one or more gene(s) of interest.

In a preferred embodiment, the viral component is a viral particle. In the context of the invention the term "viral particle" is understood to include complete virions as well as viral-like particles that have a size and/or capsid composition that are identical or similar to that of the corresponding wild type virion but do that do not contain have the complete viral genome or contain no nucleic acids and/or that lack (the full complement of) viral core proteins (such e.g. nucleoproteins).

Viral components that may be used in a method or composition of the invention preferably are from viruses selected from the group consisting of the Picornaviruses and negative-stranded ssRNA viruses including Orthomyxoviruses and Paramyxoviruses.

A preferred Picornavirus is an *Enterovirus.*

Enteroviruses are members of the picornavirus family, a large and diverse group of small RNA viruses characterized by a single positive-strand genomic RNA. All enteroviruses contain a genome of approximately 7,500 bases and are known to have a high mutation rate due to low-fidelity replication and frequent recombination. After infection of the host cell, the genome is translated in a cap-independent manner into a single polyprotein, which is subsequently processed by virus-encoded proteases into the structural capsid proteins and the nonstructural proteins, which are mainly involved in the replication of the virus. The *enterovirus* genus includes the following twelve species: *Enterovirus* A (formerly Human *enterovirus* A), *Enterovirus* B (formerly Human *enterovirus* B), *Enterovirus* C (formerly Human *enterovirus* C), *Enterovirus* D (formerly Human *enterovirus* D), *Enterovirus* E (formerly Bovine *enterovirus* group A), *Enterovirus* F (formerly Bovine *enterovirus* group B), *Enterovirus* G (formerly Porcine *enterovirus* B), *Enterovirus* H (formerly Simian *enterovirus* A), *Enterovirus* J, *Rhinovirus* A (formerly Human *rhinovirus* A), *Rhinovirus* B (formerly Human *rhinovirus* B) and *Rhinovirus* C (formerly Human *rhinovirus* C). Within these twelve species are the serotypes:

Coxsackieviruses:

serotypes CV-A2, CV-A3, CV-A4, CV-A5, CV-A6, CV-A7, CV-A8, CV-A10, CV-A12, CV-A14 and CV-A16 (found under the species *Enterovirus* A).

serotypes CV-B1, CV-B2, CV-B3, CV-B4, CV-B5, CV-B6 and CV-A9 (found under the species *Enterovirus* B).

serotypes CV-A1, CV-A11, CV-A13, CV-A17, CV-A19, CV-A20, CV-A21, CV-A22 and CV-A24 (found under the species *Enterovirus* C).

Echoviruses:

serotypes E-1, E-2, E-3, E-4, E-5, E-6, E-7, E-9, E-11, E-12, E-13, E-14, E-15, E-16, E-17, E-18, E-19, E-20, E-21, E-24, E-25, E-26, E-27, E-29, E-30, E-31, E-32, and E-33 (found under the species *Enterovirus* B).

Enteroviruses:

types EV-A71, EV-A76, EV-A89, EV-A90, EV-A91, EV-A92, EV-A114, EV-A119, SV19, SV43, SV46 and BA13 (found under the species *Enterovirus* A).

types EV-B69, EV-B73, EV-B74, EV-B75, EV-B77, EV-B78, EV-B79, EV-B80, EV-B81, EV-B82, EV-B83, EV-B84, EV-B85, EV-B86, EV-B87, EV-B88, EV-B93, EV-B97, EV-B98, EV-B100, EV-B101, EV-B106, EV-B107, EV-B110 and SA5 (found under the species: *Enterovirus* B).

types EV-C95, EV-C96, EV-C99, EV-C102, EV-C104, EV-C105, EV-C109, EV-C116, EV-C117 and EV-C118 (found under the species *Enterovirus* C).

types EV-D68, EV-D70, EV-D94, EV-D111 and EV-D 120 (found under the species *Enterovirus* D).

types: EV-H1 (found under the species *Enterovirus* H).

types: SV6, EV-J103, EV-J108, EV-J112, EV-J115 and EV-J121 (found under the species *Enterovirus* J).

Human rhinoviruses:

types HRV-A1, HRV-A2, HRV-A7, HRV-A8, HRV-A9, HRV-A10, HRV-A11, HRV-A12, HRV-A13, HRV-A15, HRV-A16, HRV-A18, HRV-A19, HRV-A20, HRV-A21, HRV-A22, HRV-A23, HRV-A24, HRV-A25, HRV-A28, HRV-A29, HRV-A30, HRV-A31, HRV-A32, HRV-A33, HRV-A34, HRV-A36, HRV-A38, HRV-A39, HRV-A40, HRV-A41, HRV-A43, HRV-A44, HRV-A45, HRV-A46, HRV-A47, HRV-A49, HRV-A50, HRV-A51, HRV-A53, HRV-A54, HRV-A55, HRV-A56, HRV-A57, HRV-A58, HRV-A59, HRV-A60, HRV-A61, HRV-A62, HRV-A63, HRV-A64, HRV-A65, HRV-A66, HRV-A67, HRV-A68, HRV-A71, HRV-A73, HRV-A74, HRV-A75, HRV-A76, HRV-A77, HRV-A78, HRV-A80, HRV-A81, HRV-A82, HRV-A85, HRV-A88, HRV-A89, HRV-A90, HRV-A94, HRV-A95, HRV-A96, HRV-A98, HRV-A100, HRV-A101, HRV-A102 and HRV-A103 (found under the species *Rhinovirus* A).

types HRV-B3, HRV-B4, HRV-B5, HRV-B6, HRV-B14, HRV-B17, HRV-B26, HRV-B27, HRV-B35, HRV-B37, HRV-B42, HRV-B48, HRV-B52, HRV-B69, HRV-B70, HRV-B72, HRV-B79, HRV-B83, HRV-B84, HRV-B86, HRV-B91, HRV-B92, HRV-B93, HRV-B97, and HRV-B99 (found under the species *Rhinovirus* B).

types HRV-C1, HRV-C2, HRV-C3, HRV-C4, HRV-C5, HRV-C6, HRV-C7, HRV-C8, HRV-C9, HRV-C10, HRV-C11, HRV-C12, HRV-C13, HRV-C14, HRV-C15, HRV-C16, HRV-C17, HRV-C18, HRV-C19, HRV-C20, HRV-C21, HRV-C22, HRV-C23, HRV-C24, HRV-C25, HRV-C26, HRV-C27, HRV-C28, HRV-C29, HRV-C30, HRV-C31, HRV-C32, HRV-C33, HRV-C34, HRV-C35, HRV-C36, HRV-C37, HRV-C38, HRV-C39, HRV-C40, HRV-C41, HRV-C42, HRV-C43, HRV-C44, HRV-C45, HRV-C46, HRV-C47, HRV-C48, HRV-C49, HRV-C50 and HRV-C51 (found under the species *Rhinovirus* C).

Polioviruses:

serotypes PV-1, PV-2, and PV-3 (found under the species: *Enterovirus* C).

Preferred Enteroviruses include Coxsackie A virus, Coxsackie B virus, Echovirus and Enteroviruses 68, 69, 70, 71 and 73 (e.g. types EV-D68, EV-B69, EV-D70, and EV-A71). Most preferably the virus is a poliovirus. The viral component can comprise one or more of the polio viral serotypes 1, 2 and 3 but preferably the viral components comprise all three polio viral serotypes 1, 2 and 3. Suitable strains of serotype 1 poliovirus include but are not limited to one or more of the Sabin 1, Mahoney, Brunenders, Brunhilde, CHAT and Cox strains. Suitable strains of serotype 2 poliovirus include but are not limited to one or more of the Sabin 2, MEF-1 and Lansing strains. Suitable strains of serotype 3 poliovirus include but are not limited to one or more of the Sabin 3, Saukett H and G, and Leon strains. In a preferred embodiments the viral component is or comprises a trivalent inactivated polio vaccine such as e.g. the Salk-IPV, containing the inactivated polio viral Mahoney strain for type 1, the inactivated polio viral MEF-1 strain for type 2 and the inactivated polio viral Saukett strain for type 3, or sIPV, containing the inactivated polio viral Sabin-1, -2 and -3 strains (van Wezel et al, 1978; Montagnon et al, 1983 & 1984). VLP (Virus-like Particles) are also encompassed within the scope of the invention.

In another embodiment, the virus is a negative-stranded ssRNA virus (Mononegavirales). The negative-stranded ssRNA viruses includes the following viruses:

| | | | |
|---|---|---|---|
| *Bornaviridae:* | | | |
| | | *Bornavirus* | Borna disease virus |
| *Rhabdoviridae:* | | | |
| | | *Vesiculovirus* | *Vesicular stomatitis* Indiana virus |
| | | *Lyssavirus* | Rabies virus |
| | | *Ephemerovirus* | Bovine ephemeral fever virus |
| | | *Novirhabdovirus* | Infectious hematopoietic necrosis virus |
| *Filoviridae:* | | | |
| | | *Marburgvirus* | Lake Victoria *marburgvirus* |
| | | *Ebolavirus* | Zaire *ebolavirus* |
| *Paramyxoviridae:* | | | |
| | *Paramyxovirinae:* | | |
| | | *Rubulavirus* | Mumps virus |
| | | *Avulavirus* | Newcastle disease virus |
| | | *Respirovirus* | Sendai virus |
| | | *Henipavirus* | Hendra virus |
| | | *Morbillivirus* | Measles virus |
| | *Pneumovirinae:* | | |
| | | *Pneumovirus* | Human respiratory syncytial virus |
| | | *Metapneumovirus* | Avian *metapneumovirus* |
| *Orthomyxoviridae:* | | | |
| | | *Influenzavirus A* | Influenza A virus |
| | | *Influenzavirus B* | Influenza B virus |
| | | *Influenzavirus C* | Influenza C virus |
| | | *Thogotovirus* | *Thogoto* virus |
| | | *Isavirus* | Infectious salmon anemia virus |
| *Bunyaviridae:* | | | |
| | | *Orthobunyavirus* | Bunyamwera virus |
| | | *Hantavirus* | Hantaan virus |
| | | *Nairovirus* | Dugbe virus |
| | | *Phlebovirus* | Rift Valley fever virus |
| *Arenaviridae:* | | | |
| | | *Arenavirus* | *Lymphocytic choriomeningitis* virus |

A preferred negative-stranded ssRNA virus is a virus that belongs to the Paramyxoviridae or to the Orthomyxoviridae. A preferred virus from the Paramyxoviridae is a virus as listed above that belongs to the Paramyxovirinae or to the Pneumovirinae. The pneumovirus preferably is a Respiratory Syncytial Virus (RSV), more preferably a human or bovine RSV. The human RSV may either be a subgroup A or B virus, and preferably is a clinical isolate, more preferably an isolate that has not been extensively passaged in vitro (preferably passaged less than 10, 8, 6 or 5 times). Preferably the (human or bovine) RSV virus is a virus comprising a viral genome having a deleted or inactivated G attachment protein gene, e.g. having a mutation in its viral genome whereby the viral genome does not encode a functional G attachment protein, such as e.g. the RSV ΔG and RSV ΔG+G virions as described in WO 2005/061698 and in Widjojoatmodjo et al. 2010. Preferred viruses from the Paramyxovirinae include Rubulavirus (Mumps virus) and Morbillivirus (Measles virus).

In another embodiment, a viral component is a virus or a virion of an Orthomyxoviridae. Preferred Orthomyxoviridae is an influenza virus. The influenza virus may be an influenzavirus of the genera Influenzavirus A, B or C, of which A is most preferred. Preferred subtypes of influenza A virus include H1N1, H2N2, H3N2, H5N1, H7N7, H1N2, H9N2, H7N2, H7N3 and H10N7, including the 2009 pandemic swine origin influenza A (H1N1) virus (SOIV, or H1N1v).

The viral components are preferably present in a composition or a solution in an amount ranging from $1\times10^0$ to $7\times10^{16}$ live and/or dead or inactivated particles per ml. The number of live particles may be determined by e.g. plaque forming units, cell culture or tissue culture 50% infectious dose ($CCID_{50}$ or $TCID_{50}$) and other suitable virological assays for determining the titer of the viral component. The number of dead or inactivated particles may be determined using an assay that quantifies the amount of antigen, such e.g. protein assays, or assays that determine haemagglutination units or polio D-antigen or N-antigen units. Preferably the viral components are present in said composition or solution in an amount of at least $1\times10^1$, $1\times10^2$, $1\times10^3$, $1\times10^3$, $1\times10^4$, $1\times10^5$, $1\times10^6$, $1\times10^7$, $1\times10^8$, $1\times10^9$ or $1\times10^{10}$ $1\times10^{11}$, $1\times10^{12}$, $1\times10^{13}$ live and/or dead or inactivated particles per ml and/or in an amount of up to $7\times10^{16}$, $1\times10^{16}$, $1\times10^{15}$ live and/or dead or inactivated particles per ml.

The amount of viral components in said composition or solution can also be expressed as weight of said viral components per ml of the solution. Preferably the viral components are present in the solution in a weight/ml ranging from 1 fg/ml to 10 g/ml. More preferably, the viral components are present in said composition or solution in an amount of at least $10^{-15}$, $10^{-14}$, $10^{-13}$, $10^{-12}$, $10^{-11}$, $10^{-10}$, $10^{-9}$, $10^{-8}$, $10^{-7}$, $10^{-6}$, $10^{-5}$, $10^{-4}$, g/ml and/or in an amount of up to $10^{-3}$, $10^{-2}$, $10^{-1}$, or $10^0$ g/ml. The weight of said viral components in said composition or solution may be determined by means known in the art per se, including e.g. protein assays. The aforementioned weights of the biopharmaceutical agent may thus also be expressed as grams protein per ml to be determined in a suitable protein assay (e.g. the Bradford assay; Zor and Selinger, 1996).

In a preferred embodiment wherein the viral components present in a composition or solution are or comprise poliovirus, the amount of poliovirus in said composition or solution preferably is at least 0.01, 0.1, 1.0, or 10 DU/ml and up to 10.000, 1.000 or 100 DU/ml, wherein 1 DU is defined as described in WHO Recommendations (TRS, NO 980, Annex 2, 2014) World Health Organization WHO Technical Report series, Recommendations for the production and control of poliomyelitis vaccine (inactivated) or wherein 1 DU is defined and determined with an ELISA as described by Westdijk et al. 2011 or Ten Have et al. 2012. In an embodiment wherein the composition or solution comprising said viral components is or comprise a vaccine, preferably a multivalent poliovirus (vaccine) is present, it is understood that each polio viral serotype is present in an amount of at least 0.01, 0.1, 1.0, or 10 DU/ml and up to 10.000, 1.000 or 100 DU/ml.

In a preferred embodiment, the viral components present in a composition or solution are or comprise RSV. More preferably, the amount of RSV in said composition or solution is at least $1\times10^1$, $1\times10^2$, $1\times10^3$, $1\times10^3$, $1\times10^4$ $TCID_{50}$/ml and up to $7\times10^{16}$, $1\times10^{16}$, $1\times10^{15}$, $1\times10^{14}$ $TCID_{50}$/ml, wherein the $TCID_{50}$ for RSV is defined and determined as described by Widjojoatmodjo et al. 2010.

Aggregation

Within the context of the invention, aggregation means an interaction between components, here between viral components such as viral particles. However, aggregation also encompasses the aggregation of viral particles with material present in the composition or solution such as impurities like host cell proteins. Such interaction may be covalent or non-covalent, soluble or insoluble, reversible or irreversible. Aggregation may be encountered at any step during a process for producing viral components: during a culture step, a purification step, an inactivation and/or a formulation step. Aggregation may also be encountered once viral components have been produced. Aggregates hence formed are present as particles and current guidelines limit the number of particles that are allowed in a final lot of (bio)pharmaceuticals (US and European Pharmacopeia).

Viral components in a composition or solution could be present as soluble particles being live, dead or attenuated as indicated above. Viral components could also be present as aggregates in said composition or solution. Usually such aggregates of viral components should be removed. The presence of aggregates in a composition or solution comprising viral components may be directly assessed by quantifying the reflection or transmission properties as a function of a certain wavelength. The wavelength is comprised ranged from 200 and 1000 nm. Usually 450 or 590 nm is chosen. The optical density is preferably assessed as carried out in example 3 A decrease in optical density indicates a decrease in light scattering which corresponds with a decrease in aggregation.

Alternatively, the presence of aggregates in a composition or solution comprising viral components may be assessed by measuring the turbidity (FTU/NTU), Field flow fractioning, electron microscopy or the light scattering such as DLS or MALS. There are commercial kits available, which can be tailored for specific applications (e.g. ProteoStat from Enzo life science part# ENZ-51023-KP002).

Alternatively, the presence of aggregates in a composition or solution comprising viral components may be assessed by using size exclusion chromatography or gel-electrophoresis under non-denaturing conditions, in which product and aggregate are separated on a column or in a gel slab and quantified or in a combination of said techniques (Li Y, 2009). More background on analytical techniques for aggregation detection can be found in the following reviews Das TK 2012 and/or Wei Wang, 2005.

Availability of functional groups may be assessed by for instance ELISA or bio-sensor assay, where an increase in measurement would correspond with a decrease in aggregation. For the polio virus a fast ELISA assay based on the D-antigen epitope has been described earlier (ten Have et al. 2012). An increase of D-antigen amount indicates that more epitopes are available/accessible for the measurement indicating a decrease in aggregation.

In this context, a decrease or a prevention or a reduction in aggregation may mean:

- a decrease of optical density (for example at 590 nm) of at least 5%, 10%, 15%, 20%, 25%, 30%, 35%, 40%, 45%, 50%, 55%, 60%, 65%, 70%, 75%, 80%, 85%, 90%, 95%, 100% or more, and/or
- an increase of D-antigen amount of at least 5%, 10%, 15%, 20%, 25%, 30%, 35%, 40%, 45%, 50%, 55%, 60%, 65%, 70%, 75%, 80%, 85%, 90%, 95%, 100% or more.

Said decrease of optical density or increase of D-antigen amount is preferably assessed by comparison to the amount of aggregates present (via the assessment of for example the optical density or D-antigen amount) in a composition or solution comprising viral components wherein:

- no basic amino acid or derivative thereof has been added or
- that has been produced or is obtainable in a method wherein a basic amino acid or a derivative thereof has not been added or
- the total concentration of a basic amino acid or a derivative thereof is less than 0.01 mM.

Preferably, a composition or a solution comprising viral components is optically or visually clear, indicating that most material is in solution and that almost no aggregates are present. More preferably said composition or solution comprising viral components is optically or visually clear for at least one, 2, 3 months.

The basic amino acids can be detected by means well known in the art per se, including e.g. photometric, fluorescence, HPLC, NMR and mass-spectometry.

Methods for Producing Composition Comprising Viral Components

In a preferred embodiment of the method for the prevention and/or reduction of the aggregation of viral components, the method is applied in or as part of a method for producing a composition comprising viral components. Accordingly, this embodiment pertains to a method for producing a composition comprising a viral component, wherein the method comprises the steps of: a) producing a medium containing the viral component; b) purification of the viral component from the medium, whereby during at least a part of the purification a basic amino acid or a derivative thereof is present at a concentration that is sufficient to prevent or reduce aggregation of the viral component; and, optionally, at least one of: c) inactivation of the viral component; and, d) formulation of the viral component, wherein the basic amino acid or a derivative thereof is as defined herein above.

Preferably in the process, the basic amino acid or a derivative thereof is maintained at a concentration that is sufficient to prevent or reduce aggregation of the viral component during or throughout the entire duration of the purification step b). More preferably, the basic amino acid or a derivative thereof is also present at a concentration that is sufficient to prevent or reduce aggregation of the viral component during at least a part of step c) and/or step d). Still more preferable, the basic amino acid or a derivative thereof is maintained at a concentration that is sufficient to prevent or reduce aggregation of the viral component during or throughout the entire duration of step c) and/or step d). Suitable concentrations of the basic amino acid or a derivative thereof for preventing or reducing aggregation of viral components are as given herein above.

Preferably in the process the viral component is a component of an *Enterovirus* as herein defined above. More preferably, the viral component are Enteroviral particles, i.e. viral particle of an *Enterovirus* as herein defined above, including virus-like particles.

Viral components and particles as identified herein are usually produced in multi-step processes. Such process may comprise the following steps:

a) a step for producing a (crude) medium comprising the viral components. This step may comprising culturing cells producing the viral components but mau also comprise steps wherein viral components are reconstituted, e.g. for producing virus-like particles. These steps may be referred to as up-stream processing steps (USP), producing a crude medium or composition from the which the viral components are to be recovered and/or purified; and b) a down-stream processing or purification step (DSP).

For IPV production (see FIG. 1), an inactivation step is carried out as step c) following step b). A formulation step (d) may also be carried out at the end of step b) or c).

These processes are known to the skilled person and could be adapted depending on the identity of the viral components to be produced.

A basic amino acid or a derivative thereof as defined herein may be added during any step (a, b, c and/or d) to aid in the processing of the product.

For example, in step a), a suitable host organism is used for replicating viral components. Such culture step leads to the production of a composition or solution comprising viral components. For IPV production suitable cells are preferably mammalian cells. Several mammalian cells are known to be a suitable substrate to replicate polioviruses for IPV production. According to the European Pharmacopoeia (6.0; 01/2008:0214), for this purpose, the virus can be propagated in human diploid cell lines (e.g. WI-38 or MRC-5), continuous cell lines (e.g. Vero), or in primary, secondary, or tertiary monkey kidney cells (MKC), or in PerC6 or in CAP cells. Poliovirus may be cultured in HeLa cells. Latest developments are described in Hamidi et al 2012.

If the virus is a poliovirus, the Vero cell line is preferred. For replicating poliovirus, the following three wild-type virulent strains are preferred: Mahoney (type 1 poliovirus), MEF-1 (type 2 poliovirus), and Saukett (type 3 poliovirus). Also other wild-type strains, like Brunhilde (type 1 poliovirus) may be used in the preparation of IPV. Alternatively, the Sabin poliovirus strains are being used for IPV manufacturing (Verdijk et al., 2011). Preferably, the cells are cultured on microcarriers as described in Van Wezel A. L., et al 1978. Preferred microcarrier is Cytodex 1.A preferred culture step for IPV is described in the experimental part. Latest developments are described in Hamidi et al 2012, Widjojoamodjo et al 2010, Thomassen et al 2013a.

In step b), the viral components are purified from the composition or solution comprising them as provide, produced or obtained in step a). There are many different ways to purify viral components depending on the identity of the virus. This purification step may be carried out by clarification, centrifugation, concentration, diafiltration, Size Exclusion Chromatography (SEC) and/or Ion Exchange Chromatography (IEC). Preferably for IPV, this purification is carried out by clarification, followed by concentration, followed by Size Exclusion Chromatography (SEC) and followed by Ion Exchange Chromatography (IEC). The clarification may be carried out on the mixture produced in step a) using filters. The concentration may be carried out using Tangential Flow Filtration (TFF), also known as Cross Flow Filtration (CFF) or Ultrafiltration (UF). A preferred purification step for IPV production is described in the experimental part and in Thomassen et al 2010 and 2013. For RSV, usually clarification may be followed by concentration, density gradient centrifugation and subsequently diafiltration using a stabilizer. For Influenza, centrifugation may be followed by filtration and concentration/diafiltration. Upon which a density gradient centrifugation step may be performed followed by an inactivation and again a diafiltration step before formulation takes place.

The process leading to a composition or solution comprising viral components may consist of two steps a) and b). Said process may comprise an additional step, called an inactivation step, step c) as explained below. In step c), after several purification steps, the viral components are inactivated. Methods for inactivating polio viral strains for safe use in vaccines are well known in the art and include, but not limited to e.g. inactivation using formalin or beta-propiolactone (see Jonges et al 2010). Said process may be followed by a formulation step (d).

Accordingly, the process or method of the invention is preferably such that the viral components are obtainable by a process comprising an up-stream processing and a down-stream processing steps and optionally an inactivation step and/or formulation step. Accordingly, a basic amino acid or derivative thereof may be used during any of these steps, preferably during the down-stream processing and/or inactivation and/or formulation steps.

A preferred production process for the poliovirus is disclosed in the experimental part.

A method of the invention may be applied for preventing the aggregation of viral components. A basic amino acid or a derivative thereof may be used in step a), step b) and/or step c) and/or step d). Preferably said basic amino acid or derivative thereof is used in step b) and/or step c). More preferably, said basic amino acid or derivative thereof is used in step b). It means that a basic amino acid or a derivative thereof may be used in any purification technique used in step b), in some of them, in all of them. Even more preferably, said basic amino acid or derivative thereof is added to the elution buffer of SEC and/or in the elution buffer of IEC. However, it is also encompassed to use a basic amino acid or a derivative thereof in any step leading to the production of a composition or solution comprising viral particles. Such steps include: harvesting step, step a), step b), step c), during the elution of capture chromatography, during the storage step of an intermediate or a final product, during the formulation step d). Preferred final concentrations of a basic amino acid or derivative have already been described herein.

Use of a Basic Amino Acid or Derivative Thereof for Preventing Aggregation of Viral Components A method of the invention may be applied for reducing the aggregation of viral components. Preferably, such viral components are obtainable by a process comprising steps a), b) and optionally c) and/or d) as described above. In such a method, a basic amino acid or a derivative thereof is added to a composition or solution comprising viral components. Thus, in one aspect, the invention pertains to the use of a basic amino acid or derivative thereof as defined herein above, for preventing or reducing aggregation of viral components, which components viral preferably are as defined herein above, more preferably the viral components are Enteroviral particles as defined herein above.

In the context of the invention, the use of a basic amino acid or a derivative thereof is said to have prevented or reduced or decreased the aggregation of viral components in a composition or solution when the use of such basic amino acid or derivative leads to a reduction or a decrease of at least 5%, 10%, 15%, 20%, 25%, 30%, 35%, 40%, 45%, 50%, 55%, 60%, 65%, 70%, 75%, 80%, 85%, 90%, 100% of the amount of aggregates in said composition or solution as assessed using the measurement of OD at 590 nm or using any other methods earlier described herein, as compared to the amount of aggregates present (for example by assessing the optical density and/or D-antigen amount) in a composition or solution comprising viral components wherein:

- no basic amino acid or derivative thereof has been added or
- that has been produced or is obtainable in a method wherein a basic amino acid or a derivative thereof has not been added or
- the total concentration of a basic amino acid or a derivative thereof is less than 0.01 mM.

In the context of the invention, the use of a basic amino acid or a derivative thereof is said to have prevented or reduced the aggregation of viral components in a composition or solution when the use of such basic amino acid or derivative leads to an increase of the titer of alive or dead or inactivated particles in solution has increased of at least 5%, 10%, 15%, 20%, 25%, 30%, 35%, 40%, 45%, 50%, 55%, 60%, 65%, 70%, 75%, 80%, 85%, 90%, 100% compared to the titer of representative live or dead or inactivated particles in solution when no basic amino acid or derivative thereof has been used. The titer is assessed as earlier described herein.

In the context of the invention, the use of a basic amino acid or a derivative thereof is said to have prevented or reduced the aggregation of viral components as IPV in a composition or solution when the use of such basic amino acid or derivative leads to an increase of at least 5%, 10%, 15%, 20%, 25%, 30%, 35%, 40%, 45%, 50%, 55%, 60%, 65%, 70%, 75%, 80%, 85%, 90%, 100% of polio D-antigen units by comparison to the number of polio D-antigen units before the addition of said basic amino acid or derivative thereof.

Composition Comprising Viral Components

In another aspect, there is provided a composition or solution comprising viral components. A "composition comprising viral components" in accordance with the invention is understood to include solutions, preferably aqueous solution, in accordance with the invention comprising viral components. A composition comprising viral components can be obtainable or obtained in a method as earlier identified herein. A preferred composition comprising viral components is obtainable in a method of the first aspect as earlier defined herein. However, compositions comprising viral components obtained in other methods than those of the present invention are expressly included herein. The viral components in the composition preferably are viral components as defined herein above. Preferred viral components in the composition of the invention are components, preferably particles, of negative-stranded ssRNA viruses, including viruses that belongs to the Paramyxoviridae or to the Orthomyxoviridae. A preferred virus from the Paramyxoviridae is a virus (as listed above) that belongs to the Paramyxovirinae or to the Pneumovirinae. Preferred viruses from the Pneumovirinae (pneumoviruses) is a Respiratory Syncytial Virus (RSV), more preferably a human or bovine RSV. The human RSV may either be a subgroup A or B virus. Preferred viruses from the Paramyxovirinae include Rubulavirus (Mumps virus) and Morbillivirus (Measles virus). In another embodiment, the viral components in the composition are components, preferably particles, of a virus that belong to the Orthomyxoviridae. A preferred Orthomyxoviridae is an influenza virus including influenzaviruses of the genera Influenzavirus A, B or C, of which A is most preferred. Preferred subtypes of influenza A virus include H1N1, H2N2, H3N2, H5N1, H7N7, H1N2, H9N2, H7N2, H7N3 and H10N7, including the 2009 pandemic swine origin influenza A (HINT) virus (SOIV, or H1N1v).

In a first embodiment, the composition comprising viral components comprises a basic amino acid or a derivative thereof, as herein defined above, in a total concentration as is specified herein above.

In second embodiment, said composition comprises a basic amino acid or a derivative thereof, as herein defined above, in a total concentration that is higher than the total concentration of a basic amino acid or derivative thereof present in a medium, preferably a culture medium. In this context, "higher" means at least 1%, 5%, 10%, 15%, 20%, 25%, 30%, 35%, 40%, 45%, 50%, 55%, 60%, 65%, 70%, 75%, 80%, 85%, 90%, 95%, or 100% higher or 5, 10, 20, 50 or 100 fold higher. A preferred culture medium is M199 as used in the experimental part. Such a medium has a total concentration of basic amino acids or derivative thereof of 0.81 mM: 0.33 mM L-arginine, 0.1 mM histidine and 0.38 mM L-lysine. The identity and possible concentrations of a basic amino acid or derivative thereof in a culture medium may vary. In an embodiment, a composition or solution of the invention comprises a basic amino acid or a derivative thereof in a total concentration which is higher than 0.81 mM. Said total concentration may be higher than 0.85 mM, 0.90 mM, 0.95 mM, 1 mM, 1.1 mM, 1.2 mM, 1.3 mM, 1.4 mM, 1.5 mM, 1.6 mM, or higher than 1.7 mM. Such a composition or solution may comprise viral components, a basic amino acid or a derivative thereof as earlier defined herein and any other possible molecule usually present in such a composition or solution. Such molecule includes a buffer as earlier defined herein and/or any other molecule usually present in a culture medium.

In a third embodiment, said composition or solution comprises a basic amino acid or a derivative thereof, viral components both as identified herein and does not comprise a buffer as earlier defined herein. Such a buffer is usually present in a culture medium. A preferred buffer component which is not comprised in said composition or solution is phenol red.

In a fourth embodiment, there is provided a composition or solution consisting of or consisting essentially of viral components and a basic amino acid or a derivative thereof in a total concentration of at least 0.01 mM. Preferably said composition or solution consists of or essentially consists of viral components and at least 0.02 mM, 0.025 mM, 0.03 mM, 0.04 mM, 0.05 mM, 0.06 mM, 0.07 mM, 0.08 mM, 0.09 mM, 0.1 mM, 0.2 mM, 0.3 mM, 0.4 mM, 0.5 mM, 0.6 mM, 0.7 mM, 0.8 mM of a basic amino acid or a derivative thereof. The identity of said basic amino acid or a derivative thereof and of the viral components present in this composition or solution has already been defined herein. Such composition or solution preferably does not comprise any other molecule than the ones specifically identified herein: the viral components, the basic amino acid or derivative thereof and, optionally, water.

In an embodiment, in any of the composition or solution identified herein, the formation of viral aggregates is reduced compared to the formation of viral aggregates in a corresponding composition not comprising said basic amino acid or derivative thereof. In this context, reduced means a reduction or a decrease of at least 5%, 10%, 15%, 20%, 25%, 30%, 35%, 40%, 45%, 50%, 55%, 60%, 65%, 70%, 75%, 80%, 85%, 90%, 95% or 100% of the amount of viral aggregates formed compared to the amount of viral aggregates in a corresponding composition not comprising said basic amino acid or derivative thereof. This reduction may be observed over a period of at least 1 min, 1 hour, 6 hours, 24 hours, 48 hours, 72 hours, one week or longer.

Preferably, any composition or solution as provided herein is for use as a prophylactic or therapeutic substance/medicament, more preferably for inducing an immune response in an individual against said viral components. This composition may be further formulated and may be called a formulation or pharmaceutical composition and is for use as a prophylactic or therapeutic substance/medicament, more preferably for inducing an immune response in an individual against said viral components.

For use as a prophylactic or therapeutic substance/medicament the formulation can be used as liquid formulation (suspension) as dried formulation or it can be reconstituted by dissolving the dried formulation, e.g. using water or other suitable liquid. The formulation is preferably reconstituted to its original volume, i.e. the volume before drying. Preferably the formulation is a formulation for inducing an immune response (in an individual) against a disease or an infectious disease or cancer. It is understood that the individual or subject to whom the formulations of the invention are administered can be a human but can also be an animal, such as a farm animal or pet, including e.g. mammals (herbivores, carnivores and omnivores), birds, reptiles, (like livestock, poultry, cattle, bovines, pig, cats). More preferably, the formulation is a formulation for vaccination against an (infectious) disease. The formulation is thus preferably a formulation for the prevention or treatment of an infectious disease. In another embodiment the invention relates to the use of the formulation obtainable or obtained in a method according to the invention as described herein above for the manufacture of a medicament for inducing the immune response, for vaccination and/or for the prevention or treatment of an infectious disease. In yet another embodiment, the invention relates to a method for inducing an immune response against an infectious agent by administering an effective amount of the formulation to a subject in need thereof. The immune response is preferably induced against an antigen present in the viral components. The antigen preferably is an antigen of a pathogen causing the infectious disease or an antigen that induces an immune response against the pathogen. The pathogen preferably is a virus as herein defined above. The formulation of the invention can be administered with or without reconstitution via intranasal, parenteral, intramuscular, subcutaneous and/or transdermal routes.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

For ease of use, the term IPV in this document, is used to encompass both the final product as well as it's (process) intermediates, which are not yet inactivated.

All patent and literature references cited in the present specification are hereby incorporated by reference in their entirety.

The following examples are offered for illustrative purposes only, and are not intended to limit the scope of the present invention in any way.

BRIEF DESCRIPTION OF THE FIGURES

FIGS. 2C, 2D and 2E depict the effect of respectively three different basic amino acids (L-arginine, L-lysine and L-histidine) on aggregation of three different influenza strains (Influenza A/Uruguay H3N2 (NIBSC) Influenza B/Florida/4/2006 (NIBSC) and Influenza A/PR/8/34 (NIBSC)). In FIGS. 2F, 2G and 2H depict the effect of respectively three different basic amino acids (L-arginine, L-lysine and L-histidine) on aggregation of three different poliovirus (Sabin) subtypes 1, 2 and 3.

EXAMPLES

Example 1

Virus Production

Figure 1:
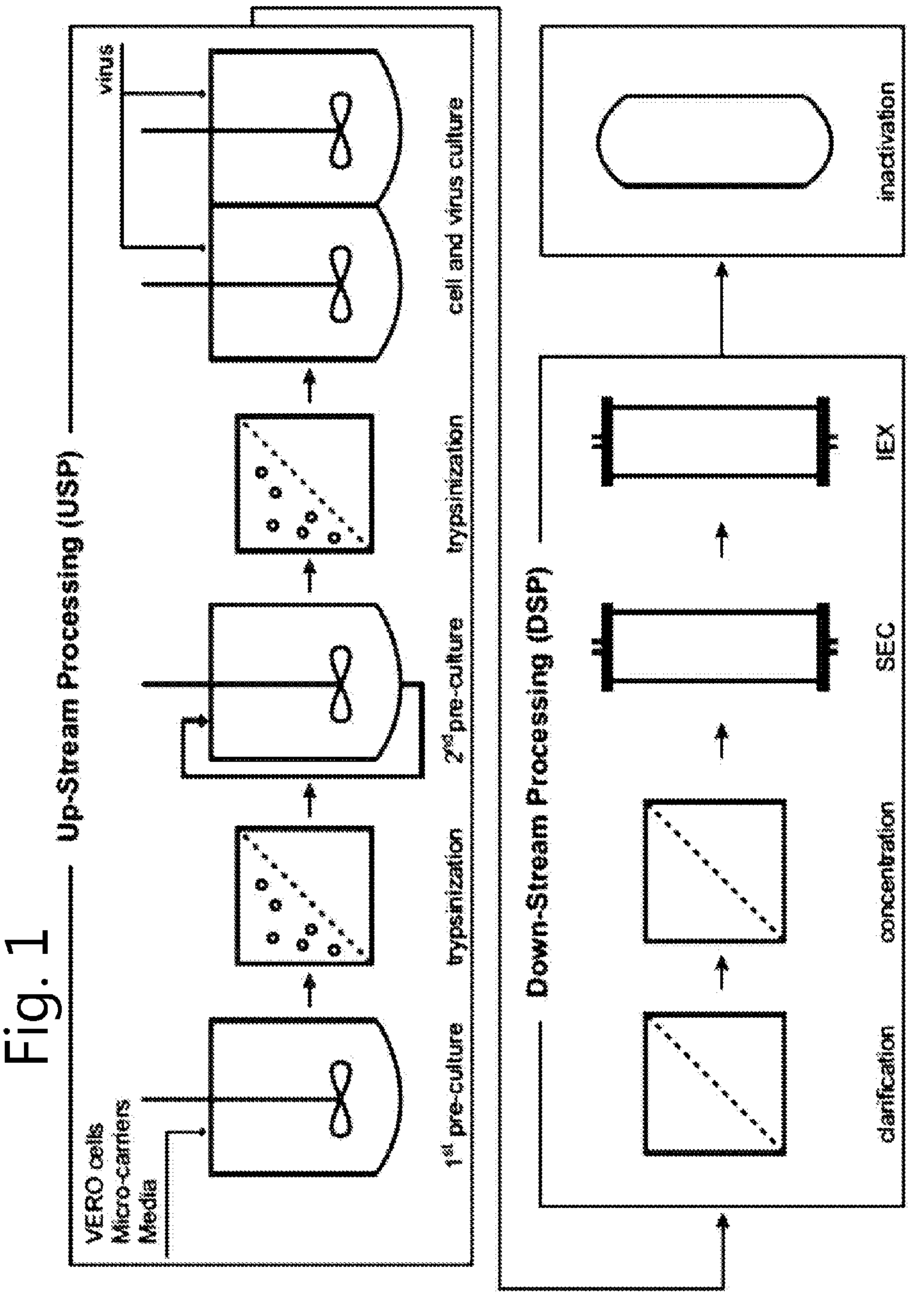
FIG. 1: Schematics of the inactivated polio vaccine production process. During upstream processing cells are expanded using two pre-culture steps prior to cell culture and virus culture. The downstream processing consists of clarification, concentration, size exclusion chromatography and ion exchange chromatography followed by inactivation. To obtain trivalent polio vaccine this procedure is followed for each polio virus type separately prior to mixing for end product formulation (Bakker, 2011).

Cell culture at lab-scale. Use of different systems. Production of inactivated attenuated poliovirus strains at lab-scale.

The process starts with the cultivation of Vero Cells. The VERO cell line originates from African green monkey kidney cells (MKC) (ATCC CCL-81). Cultures are started with an ampoule from a well characterized frozen cell bank. To acquire the proper amount of cells to inoculate a bioreactor, a seed train with monolayer cultures in TC-flasks is started with M199 medium containing 5% Foetal bovine serum. M199 medium is as described in Morgan J. F. et al (1955) or Morgan J. F. et al (1950). It comprises mM amounts of basic amino acids: L-Arginine 0.33 mM, L-Histidine 0.1 mM, L-Lysine 0.38 mM (http://www.invitrogen.com/site/us/en/home/support/Product-Technical-Resources/media_formulation.86.html).

The seed train is continued with sub cultivations in four T-flasks, three Hyper flasks and three Cell factories. The Cell factories have a total surface area of 3*6320 $cm^2$. Cells are detached by trypsinisation. The entire seed cultivation takes about 2 weeks.

VERO cell (earlier primary MKC was used) cultivation in bioreactors is performed on micro carriers (Cytodex 1 GE Healthcare, product number 17-0448-**). This technique was developed at RIVM in the late 1960's by van Wezel (1978). The microcarriers provide a large surface area for the attachment of Vero cells. The cultivation on micro carriers starts in batch mode in a 5 L (liter) bioreactor (3 L working volume). The 5 L bioreactor is operated with 3 L E-MEM cultivation medium supplemented with bovine serum (BS) (Minimum Essential Medium Eagle, Sigma Aldrich, M4642). The bioreactor is prepared with 4 g/L Cytodex 1 micro carriers and E-MEM cultivation medium. When cultivation conditions are stable, the bioreactor is inoculated with cells from the seed train to an initial cell concentration of $0.8*10^6$ cells/ml. The cultivation starts in batch mode for 1 day and is continued in recirculation mode for 3 days with 12 L E-MEM medium in the recirculation bottle. In recirculation mode cells start growing in multi layers. This way cell concentration of $4.0\text{-}4.5*10^6$ cells/ml can be reached in the 5 L bioreactor.

Cells are detached from the micro carriers by trypsinisation. The released cells are used to start a cell culture in a 20 L. The 20 L bioreactor is prepared with 3 g/L micro carriers and E-MEM cultivation medium supplemented with BS. The final working volume after inoculation is 16 L. The inoculation level is $0.2*10^6$ cells/ml. The 20 L bioreactor is operated in batch mode. Cultivation takes 3-4 days depending on the lag phase after transfer of cells from the 5 L bioreactor to the 20 L bioreactor. Metabolites like glucose and glutamine are monitored to check if feeding of glucose or glutamine is necessary to maintain optimal growth conditions.

Virus propagation is performed in the 20 L bioreactor. A medium switch from E-MEM to M199 is performed to create favorable conditions for virus propagation. The temperature is lowered from 37° C. to 32.5° C. Dissolved Oxygen percentage (DO %) is lowered from 50% to 25%. The multiplicity of infection level (MOI) is 0.01. Virus propagation and lysis take 3-5 days dependent on the virus subtype. Virus propagation and lysis are monitored by microscopic inspection of the Cytopathological effect (CPE). The virus culture is finished when the CPE is ≥90% and/or when oxygen consumption has ceased and at that time can be harvested for purification (down-stream processing, DSP).

The bioreactor contains a steel 75 μm mesh filter to retain microcarriers in the reactor. The virus harvest, containing cell debris, is clarified by two disposable filters in series. The depth filter cassette has incorporated of diatomaceous earth (HC Pod Filter grade COHC Millipore # MCOHC054H1). The final filter is a dual layer 0.5/0.2 μm filter (Millipore Express SHC opticap XL #KHGES015FF3).

The concentration step in the polio production process is performed by Tangential Flow Filtration (TFF) (also known as Cross Flow Filtration (CFF) or Ultrafiltration (UF)). The total concentration factor is 700-800. To avoid high losses of product in the dead volume of the TFF system, two systems are used in succession. Both systems use 100 kD flat screen filter cassettes (0.2 $m^2$ and 50 $cm^2$ resp.) Virus particles are retained and small molecules end up in the filtrate and are removed.

Size Exclusion Chromatography (SEC) is a purification technique that separates particles and molecules by size. Large molecules elute faster than smaller ones. The column is packed with CL6B from GE healthcare. The first peak might contain aggregates and high molecular weight molecules like Host Cell Proteins (HCP's). The second peak is the product peak with most of the poliovirus. During SEC, the poliovirus particles eluted with a phosphate buffer with low ionic strength (20 mM) pH 7.0±0.2.

Ion Exchange Chromatography (IEX) is preferably performed with a DEAE-ligand based matrix, Sephadex A50 from GE Healthcare. This particular resin is supplied as a dry powder from the supplier and, needs to be prepared by the user. This involves swelling and rinsing of the resin, column packing and column equilibration. The aim of this unit operation is to bind negatively charged components to the matrix. RNA/DNA/Host Cell Proteins are the main components that are bound to the column matrix. The poliovirus has limited interaction with the matrix.

The purified virus obtained from the ion exchange chromatography is stabilized and diluted to a specific strength (when applicable). Stabilization and dilution is performed with M199 medium. The required concentration depends on the virus type Finally Glycine is added to a final concentration of 5 g/L in preparation of the inactivation The stabilized, diluted and prepared purified virus is inactivated using formaldehyde in a final concentration of 2-3 mM (or 1:4000). Inactivation takes 13 days and is performed at a temperature of 37° C. After 6-8 days of inactivation an intermediate filtration is performed to remove possible aggregates.

After 13 days of inactivation the sterile monovalent pool is ready for storage at 2-8° C. At this point the obtained inactivated poliovirus is called monovalent bulk Mixing/Formulation A bulk is prepared by mixing the required serotypes together in the pre-determined concentrations. This can be either a single (type 1, type 2 or type 3), bi/divalent (type 1 and type 2 or type 1 and type 3 or type 2 and type 3) or trivalent mixture (type 1 and type 2 and type 3) formulation. Furthermore, the formulation can be combined with other vaccines like, Diphteria, pertussis, tetanus, Hepatitis, *Haemophilus*, meningitis, pneumococcal and/or others.

Optimized Process

The optimized process follows the same procedure as stated above with the following deviations:

- Clarification step is flushed with medium, after product filtration is finished
- The $2^{nd}$ filter in the concentration step is not a 50 $cm^2$ 100 kD cassette filter, but a 115 $cm^2$ hollow fiber is used as $2^{nd}$ 100 kD filter (Spectrum labs # D02-E100-05-N).
- The buffer during the SEC is changed to a phosphate buffer supplemented with a basic amino acid like L-arginine at pH 7.0±0.2.
- During Ion exchange chromatography the buffer used for preparing the matrix and eluting the product is changed to a phosphate buffer supplemented with a basic amino acid like L-Arginine at pH 7.0±0.2.

The improved process gives a higher D-antigen yield (DU/ml) (with comparable or better immunogenicity as can be assayed by a poliovirus neutralizing cell culture assay on sera from immunized rats (FIGS. 3A, 3B, 3C and 3D).

In Table 1 the recoveries (percentages based on D-antigen yield) for the current and the optimized process (modification by addition of a basic amino acid) are given, as well as the total process yield for poliovirus types 1 and 2. The antigenicity of the polio virus or IPV product was tested using a polio D-antigen ELISA (ten Have et al. 2012).

TABLE 1

Comparison of poliovirus yields as observed for the current and the improved purification process:

| | Process step yield (%) | | | |
|---|---|---|---|---|
| | Current | | with added L-Arginine | |
| Process step | Poliovirus subtype 1 | Poliovirus subtype 2 | Poliovirus subtype 1 | Poliovirus subtype 2 |
| SEC | 69 ± 2.1 | 51 ± 0.8 | 77 ± 6.0 | 70 ± 3.8 |
| IEX (DEAE) | 94 ± 19.2 | 32 ± 4.5 | 93 ± 8.3 | 82 ± 7.1 |
| Overall | 40 ± 1.5 | 4 ± 0.9 | 54 | 27 |

Example 2

Reduction of Aggregate Level

Reduction of virus aggregation can be achieved by addition of a (concentrated) solution of a basic amino acid or derivative. Any skilled person can fine-tune this method to their specific need. See FIGS. 2A and 2B.

In a further experiment, stock solutions of basic amino acids were prepared and added to batches containing different viruses in an aggregated form. Solutions were added in a 1:1 ratio. Aggregation was measured as the absorbance at 590 nm (Biowave DNA, WPA). Aggregated virus as measured prior to the addition of basic amino acids was set at 100%. The effects of different concentrations of amino acid addition on the percentage of aggregated virus are shown in FIGS. 2C, 2D and 2E for the effects of three different basic amino acids L-Arginine, L-Lysine and L-Histidine respectively) on three different influenza strains (Influenza A/Uruguay H3N2 (NIBSC), Influenza B/Florida/4/2006 (NIBSC) and Influenza A/PR/8/34 (NIBSC)). In FIGS. 2F, 2G and 2H results are depicted for the effect of respectively three different basic amino acids (L-arginine, L-lysine and L-histidine) on three different polio (Sabin) subtypes 1, 2 and 3.

Example 3

Offline Additions (Dissolving Existing Aggregation)

Aggregated virus was produced according to the slightly modified Salk-IPV production protocol with a 20 mM phosphate buffer (Sabin batches types 1, 2 and 3; intermediate product fractions after SEC and IEX). The obtained virus fractions were frozen in −80° C. until use. The freezing positively facilitated and/or enhanced the aggregation effect.

Influenza (with aggregates) was produced using a laboratory egg based process consisting of inoculating embryonated eggs (strain: A/Uruguay/H3N2 (NIBSC)), incubating, cooling and subsequent harvesting by disk-stack centrifugation followed by depth filtration (GE Healthcare). Virus was purified by sucrose density centrifugation, followed by a β-propiolactone inactivation with filtration. Finally a diafiltration/concentration was performed.

pH is measured using a calibrated pH meter (Orion scientific), with a gel-electrode (Mettler Toledo) and corrected using either sulfuric acid or sodium hydroxide.

Optical density, as measurement of aggregation, was determined using a Biowave DNA spectrophotometer (WPA) at wavelengths 450 & 590 nm in either plastic disposable cuvettes (Greiner) or quartz cuvettes with a diameter of 10 mm.

ELISA-assay; antigenicity of the polio virus or IPV product was tested using an ELISA (ten Have et al. 2012).

The virus products, were used in offline testing with a range of concentrations of the different additives according to Table 2. The additive was weighed in a test tube and to this 1 or 2 ml of the product was added, the solution and additive were mixed. When the additives were dissolved the pH change was measured and corrected (when needed) to the initial product pH. After 1 hour the optical density was measured.

TABLE 2

Additives tested for their ability to prevent or break up aggregation of virus

| Additive | Remarks |
| --- | --- |
| L-arginine | |
| D-arginine | Chiral form of L-arginine |
| L-lysine | |
| N-α-acetyl L-arginine | Derivative of arginine |
| Agmatine Sulfate salt | Derivative of arginine |
| | Same concentration as |
| Mixture composing of: | used in medium |
| Glycine | M199 |
| Alanine | |
| l-valine | |
| l-leucine | |
| l-isoleucine | |
| l-proline | |
| hydroxy-l-proline | |
| l-serine | |
| l-threonine | |
| l-glutamic acid | |
| l-glutamine | |
| l-aspartic acid | |
| l-aspargine | |
| M199 | Cell culture medium |
| (mix of >50 components) | |

Figure 2A:
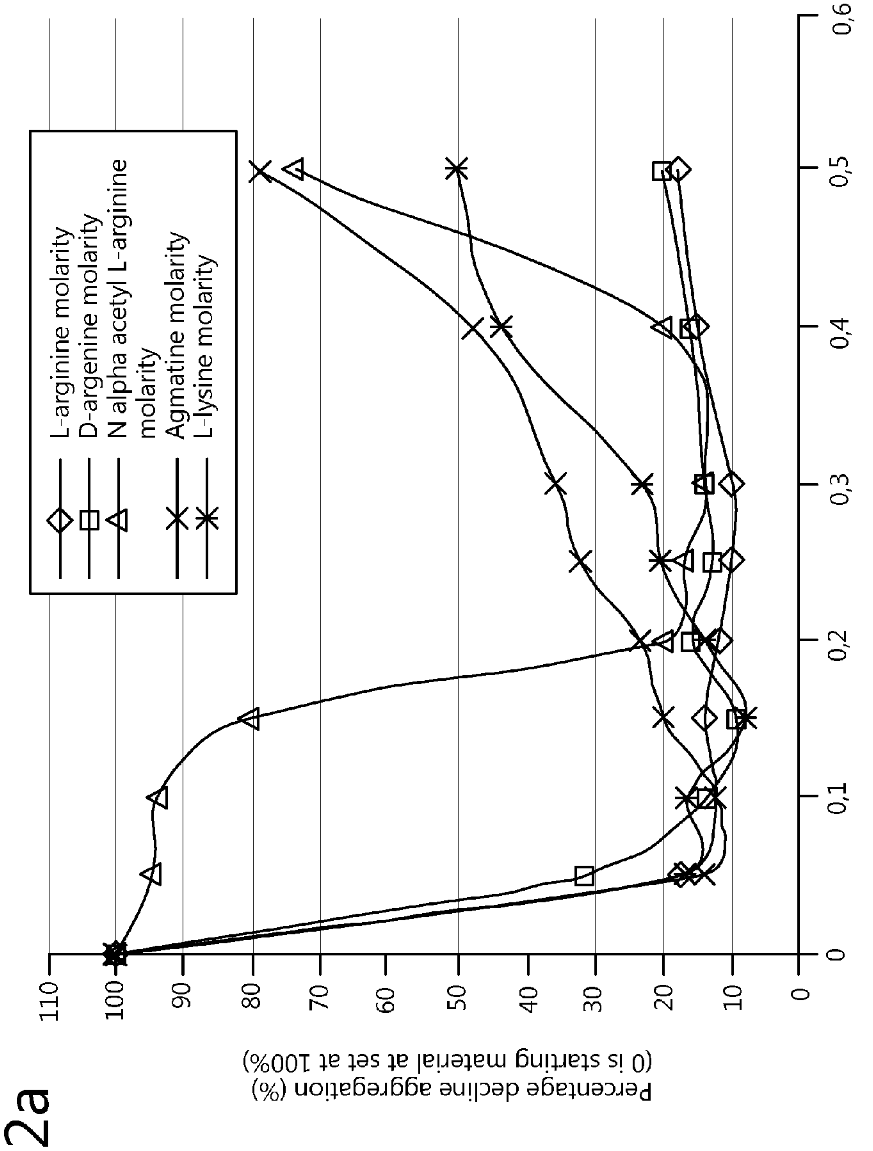
FIGS. 2A, 2B, 2C, 2D, 2E, 2F, 2G, and 2H: Effect of the addition of different basic amino acids and derivatives to solutions containing aggregated virus on breaking up the existing aggregation. No additions (0 mM) was assumed to result in the maximum aggregation and has been set at 100% aggregated virus. Reduction is shown when different additions of basic amino acids and derivatives thereof in different concentrations are used. Detection of aggregation was performed using absorbance measurements at 590 nm. Other wavelengths may be used as well, leading to different spectra. Experiments carried out in FIG. 2A have been carried out using non-enveloped polio virus, FIG. 2B with enveloped influenza virus.
Figure 2B:
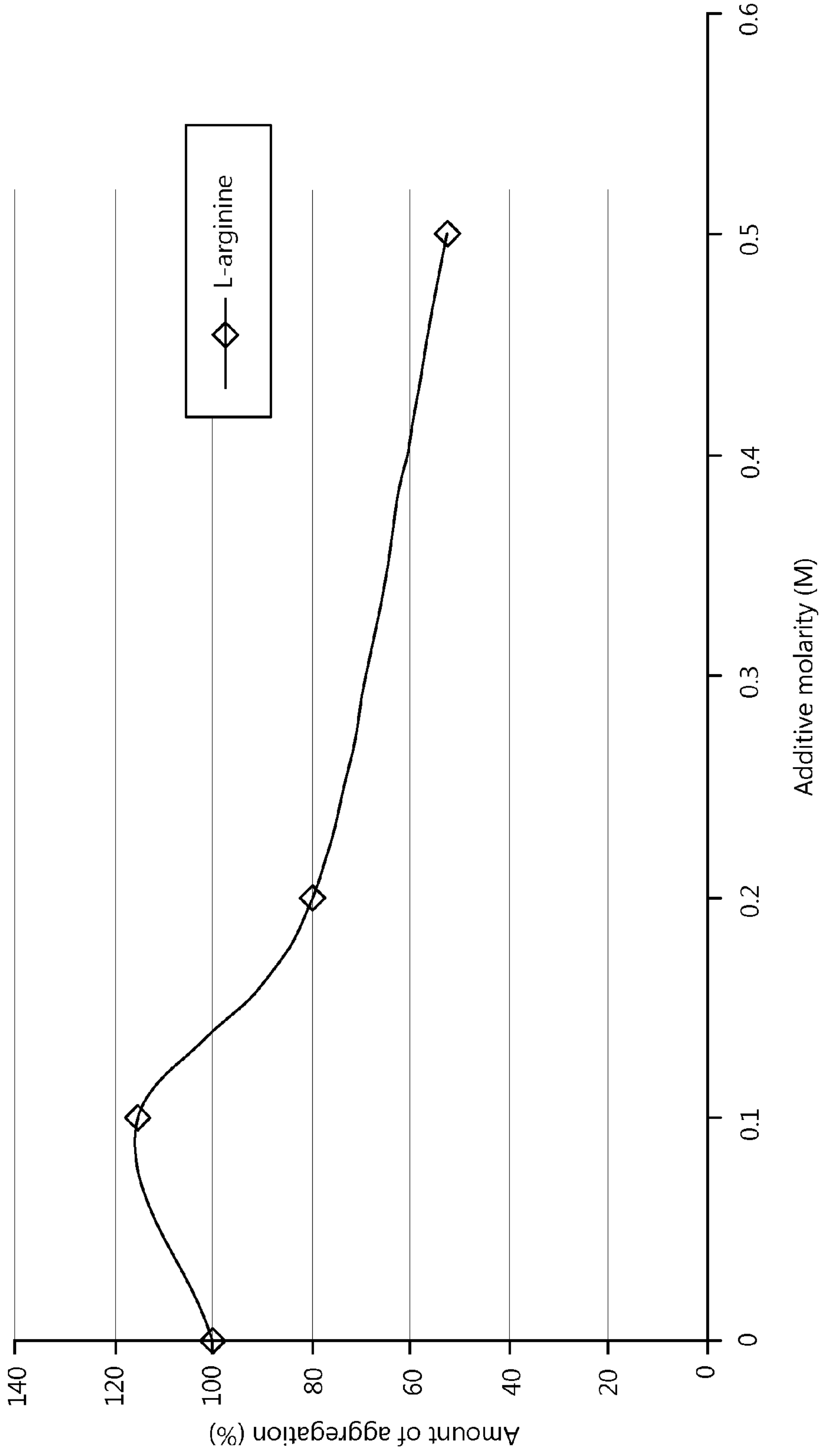
Figure 2C:
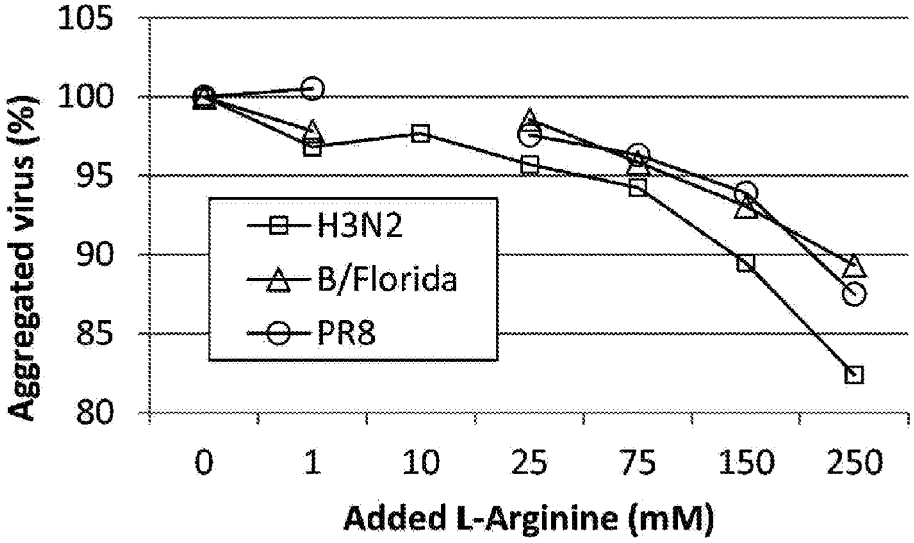
Figure 2D:
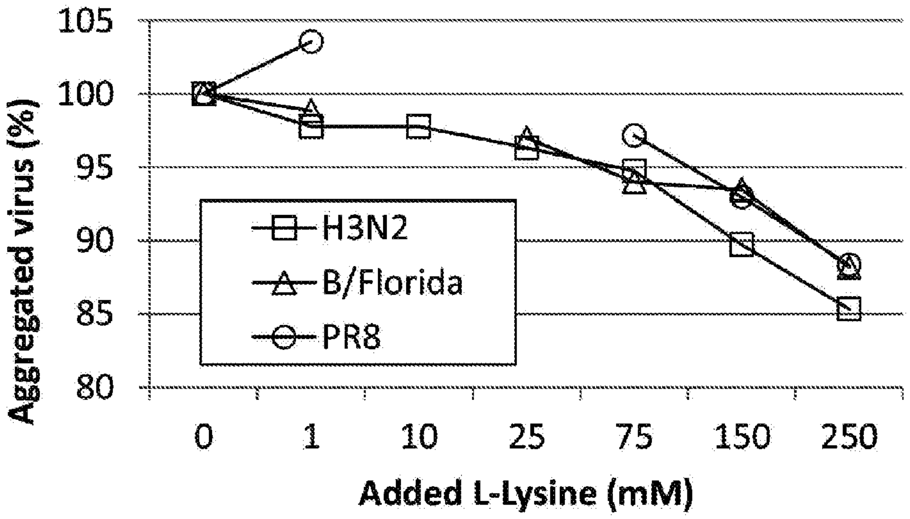
Figure 2E:
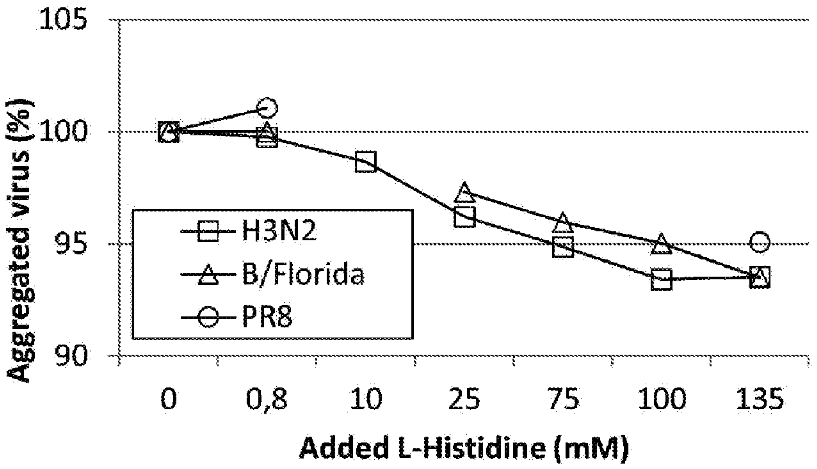
Figure 2F:
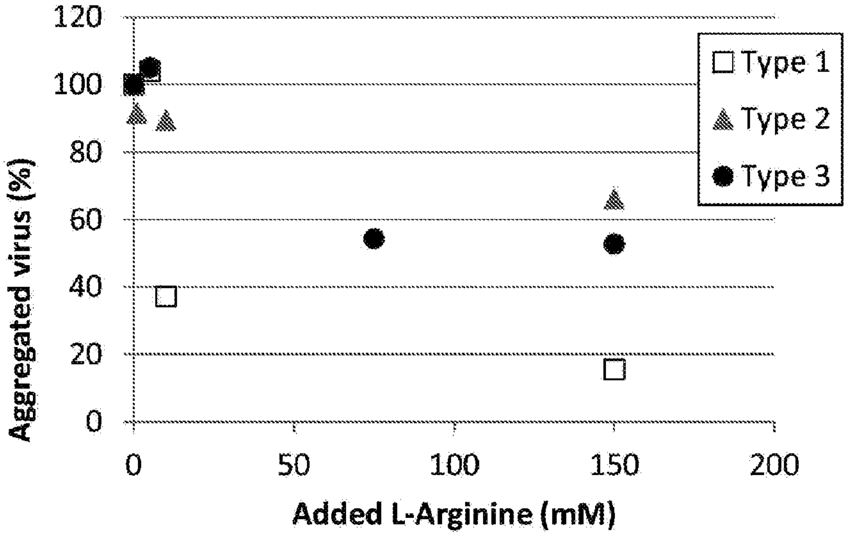
Figure 2G:
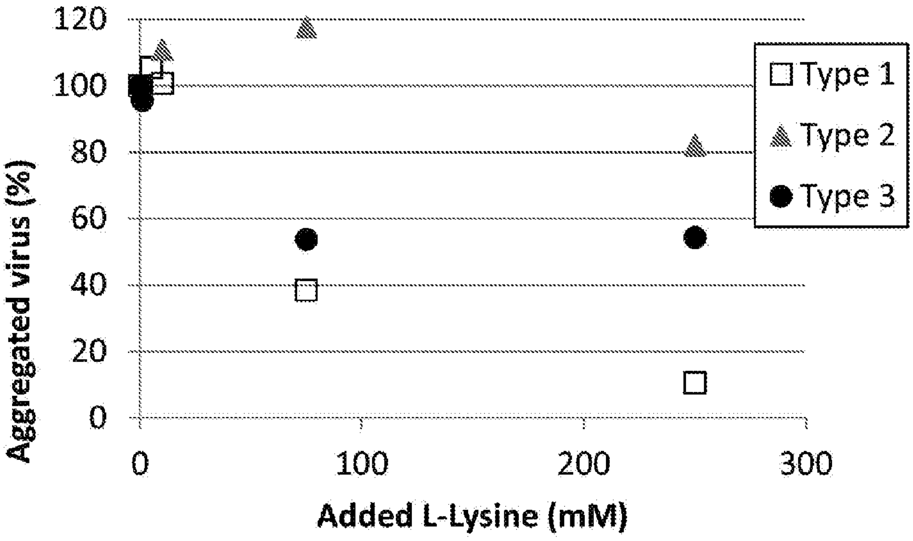
Figure 2H:
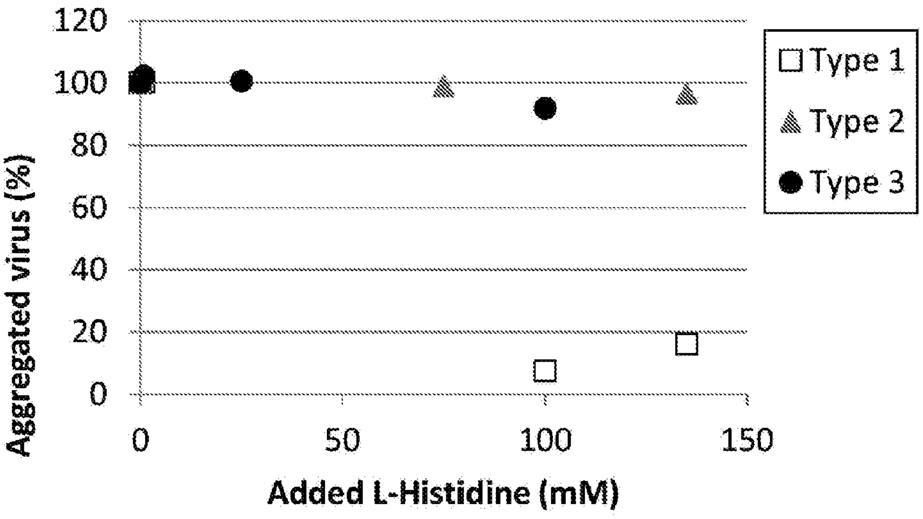
Figure 3A:
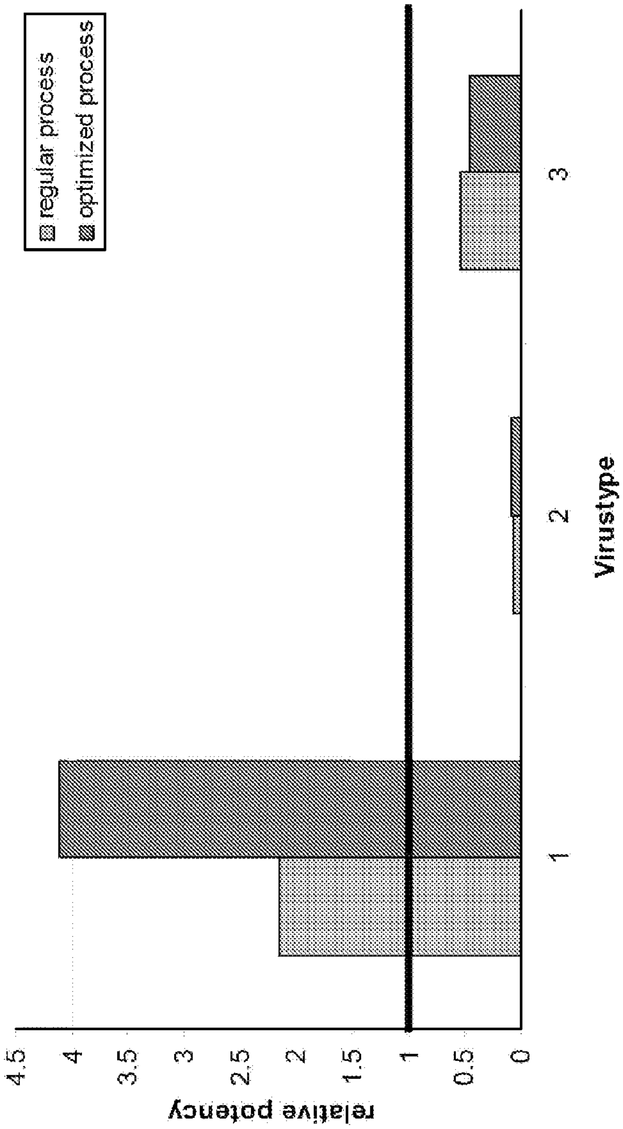
FIGS. 3A, 3B, 3C and 3D: Sabin-IPV rat potency (Albrecht P et al. 1984) using the regular IPV production process as e.g. described by Thomassen, 2013b, versus the optimized process according to the invention. Salk-IPV is used as reference standard (set at 1). Sabin-IPV prepared using the optimized process, i.e. using methods to prevent aggregation, yielded vaccines with comparable or better immunogenicity in rats compared to Sabin-IPV prepared as described by Thomassen 2013b. Salk-IPV is used as internal reference standard (set at 1).
Figure 3B:
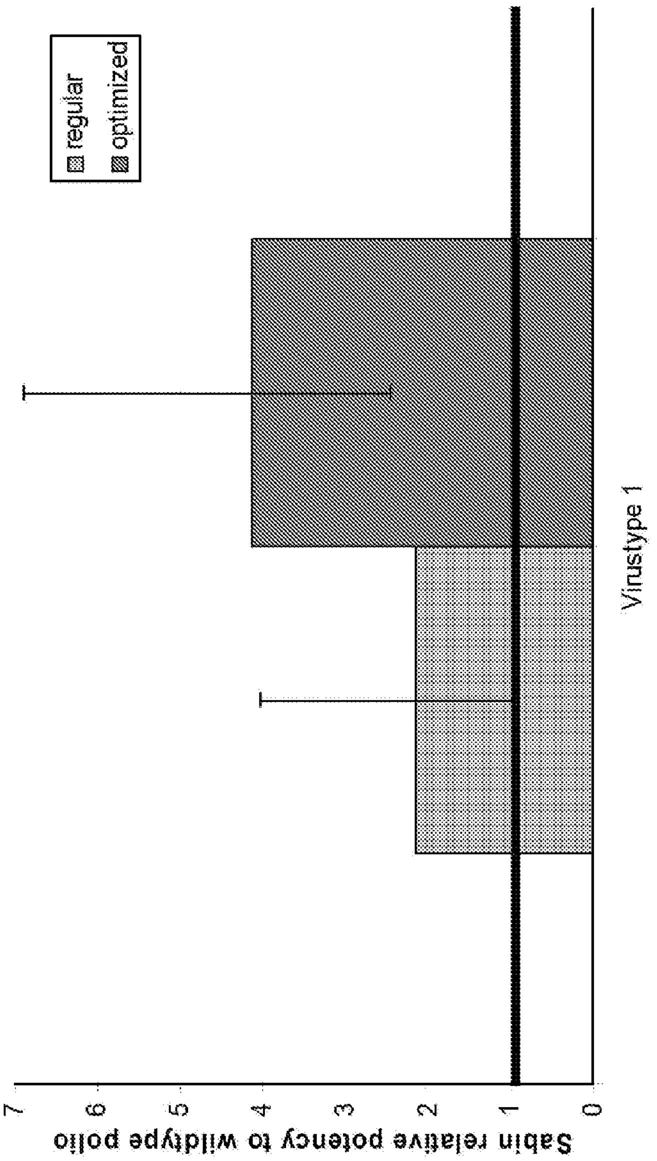
Figure 3C:
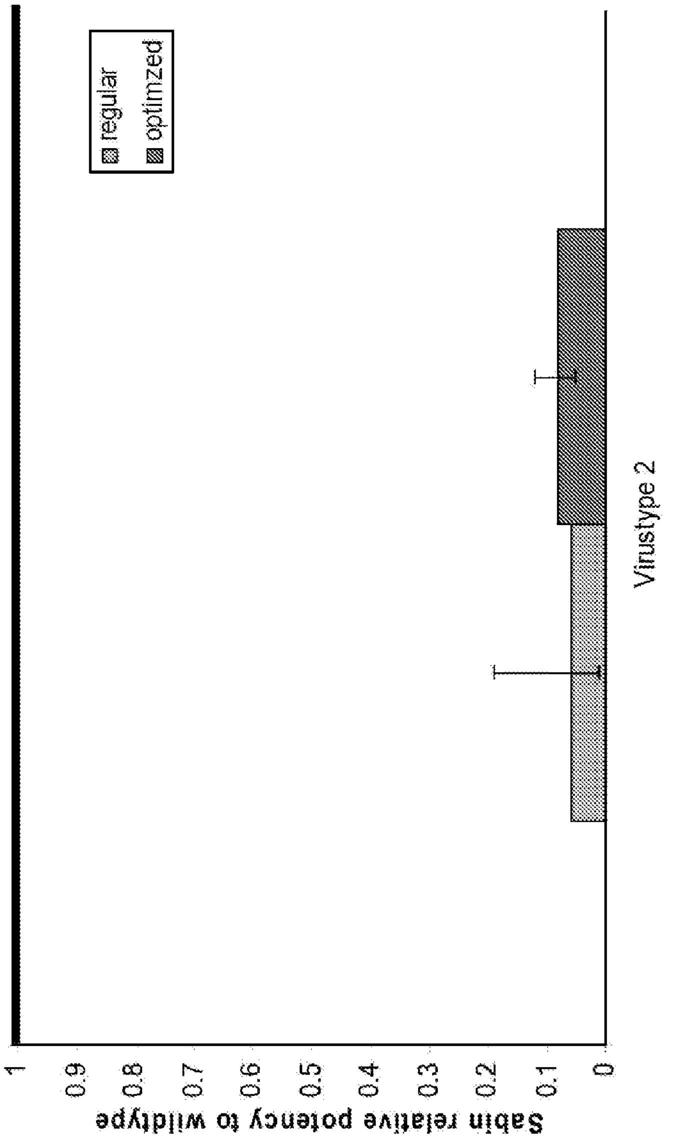
Figure 3D:
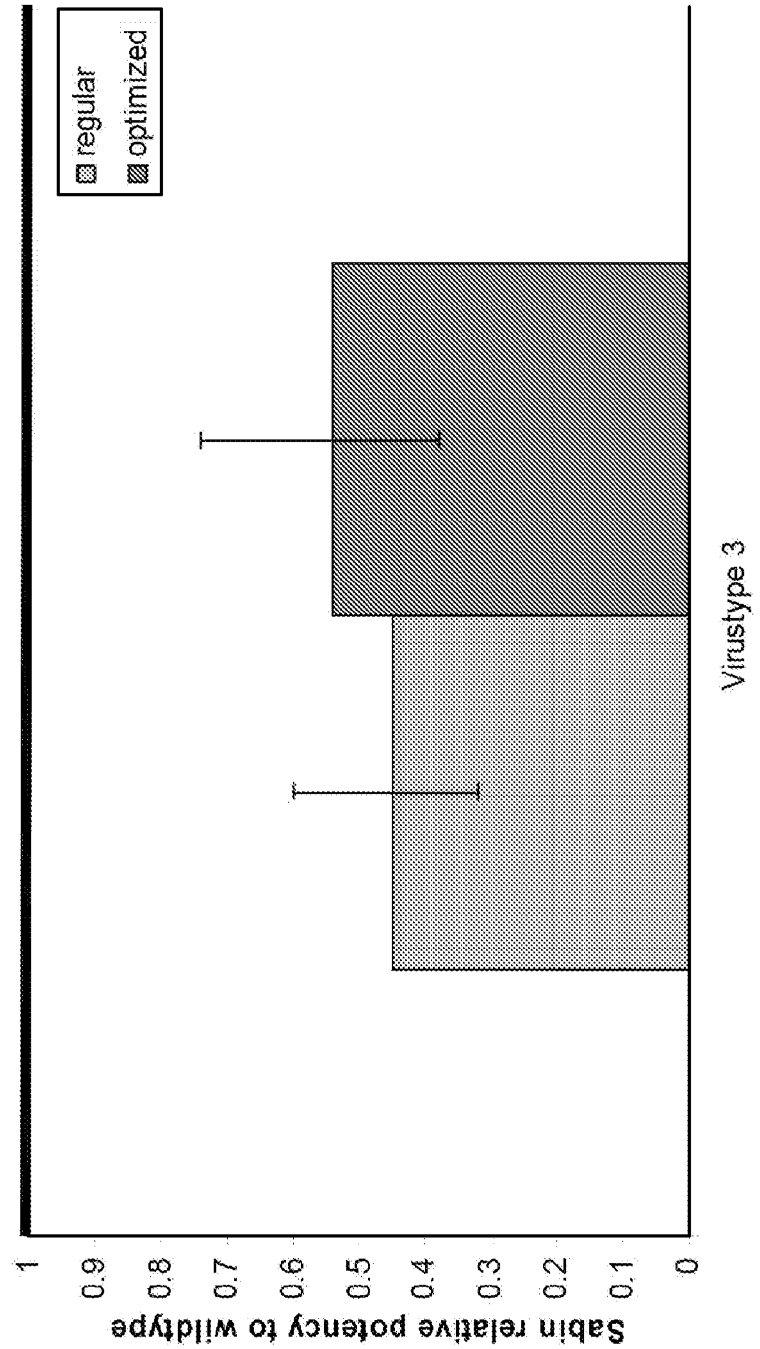

The offline additions of different additives perform differently in clearing the aggregates at different molarities and with different products (FIGS. 2A and 2B). The initial aggregated virus product was set at 100% as measured with no additions, a blank buffer solution was used as negative control e.g. no aggregation to be reached 0%.

Addition of the M199 to virus was able to clear the formed aggregates from all virus products either stored at −80° C. stored material or freshly prepared solutions. For poliovirus, this resulted in a 22% +/−12 increase of available D-antigen epitope as measured in an ELISA-assay (ten Have et al, 2012).

Example 4

Fast Purification of Influenza (Proof of Concept)

Influenza was purified as a proof-of-concept using Arginine according to the following protocol. Virus feed was prepared from harvest of 10.000 SPF (Specific Pathogen Free) embryonated hen's eggs inoculated, at day 11 with influenza A/Uruguay H3N2 virus (EID50/ml of 9.17) using a semi-automatic inoculation machine located in a down flow booth with HVAC filters. Prior to inoculation, the eggs and the needles were disinfected using 70% ethanol. The eggs were incubated during 72 hr for 3 days at 35° C. and then cooled overnight to circa 4° C., with circa 12 hr temperature effectively below 8° C. Harvest of the allantoic fluid from the decapped eggs took place with a semi-automatic harvest machine in a down flow booth. Clarification of the crude harvested allantoic solution was performed with a Westfalia disk stack separator continuous centrifuge at 65 L/h, 1 bar backpressure, 10.000 rpm, followed by filtration using two parallel 10 inch 2.0 μm GE ULTA prime capsule depth filters (GE Healthcare).

From the obtained batch approximately 3 L was separated for small scale testing.

The 3 L was again divided in 2 portions and each portion was concentrated approximately 15 times using a hollow fiber (GE Healthcare #UFP-750-E-3X2MA) and diafiltered, with 10 volumes, against either PBS (GIBCO) or PBS (GIBCO) supplemented with 0.35M L-Arginine (Sigma-Aldrich).

From the thus acquired concentrated and diafiltered material, 10 ml was tested on a size exclusion column of 90 cm bedheight (column vl11/100 Millipore) containing Sepharose 6 fast flow matrix (GE Healthcare) using either PBS or PBS supplemented with 0.35M L-Arginine using an Akta explorer chromatographic system (GE Healthcare)

All samples were inactivated using formaldehyde prior to analysis.

Analytical Assays

SRID (single radial immunodiffusion) assay is based on the reaction between the antibodies present in a flat agarose gel and the antigen that diffuses from an application spot in the gel. Once the concentration of antibody and antigen are equal a precipitation in the shape of a ring occurs. The precipitate was stained using Coomassie Brilliant Blue and the size of the ring was used as a measure for the concentration.

Ovalbumin concentration was measured using a direct sandwich ELISA (Enzyme Linked Immuno Sorbent Assay). The assay was performed according to the instructions of the supplier of the ELISA kit (Serazym Ovalbumin ELISA: Cat. No. E041C, Seramun Diagnostica GmbH Wolzig). Independent duplicates of two different dilutions were uses as samples. Samples containing the antigen were pipetted in ELISA plate wells coated with polyclonal anti-ovalbumin antibodies. Anti-ovalbumine-linked to Horse Radish Peroxidase was added, followed by washing away unbound substances. The addition of a substrate initiated the development of a blue color. This process was stopped by adding sulphuric acid; the color changed from blue to yellow. The absorption at 450 nm was a measure for the quantity. A 630 nm filter was used as reference (Biotek reader with KC-jr and KC4 software).

Results

Material collected from the chromatographic run was tested in a SRID assay for the haemagglutinin antigen content. Analysis showed an 8 percent higher haemagglutinin antigen content in the material supplemented with 0.35 m L-Arginine.

Furthermore the concentrated and diafiltrated (UF/DF) material from the hollow fiber which contained the supplemented L-Arginine mono hydrochloride contained significantly less (upto 76%) ovalbumine present in the sample, indicating that the diafiltration was far more efficient in removing impurities in presence of L-Arginine mono hydrochloride.

Example 5

Effect of Additions to Poliovirus Chromatography

Breaking up aggregation after it has occurred is one way of solving the problem. However, during manufacturing it is more important to prevent the aggregation from the beginning. During the processing of (polio) virus, formed aggregates are removed during SEC and bind as impurities to the IEX (DEAF) column leading to high product losses (up to 70%).

The chromatographic separations were performed in different solutions according to Table 3. The starting material is the concentrated poliovirus either from the −80° C. freezer or freshly prepared. Only the L-Arginine HCL addition to the 20 mM phosphate buffer was tested during chromatographic separations next to the control.

The yield (in terms D-antigen recovery) was determined, the results are given in Tables 4 and 5 (nd=not done).

TABLE 3

| Chromatography additions | | | |
|---|---|---|---|
| | Control | Alternative 1 | Alternative 2 |
| SEC | 20 mM phosphate pH 7.0 | M199 | 20 mM phosphate + 150 mM L-Arginine pH 7.0 |
| IEX | 20 mM phosphate pH 7.0 | M199 | 20 mM phosphate + 150 mM L-Arginine pH 7.0 |

TABLE 4

SEC (size-exclusion column chromatography) recovery (percentage (%) based on D-antigen per milliliter) result with different elution buffers Poliovirus Recovery (%)

| Batch | Poliovirus type | Control: Phosphate buffer | Alternative 1: M199 | Alternative 2: L-Arginine |
|---|---|---|---|---|
| 1 | 1 | 30 | 16 | 73 |
| 2 | 1 | 67 | nd | 81 |
| 3 | 2 | 72 | 59 | 66 |
| 4 | 2 | 66 | nd | 69 |
| 5 | 3 | 71 | 64 | 58 |
| 6 | 3 | 75 | nd | 73 |
| 7 | 3 | 83 | nd | 68 |

TABLE 5

Ion-exchange column chromatography) recovery (percentage (%) based on D-antigen per milliliter) results with different elution buffers Poliovirus recovery (%)

| Batch | Poliovirus type | Control: Phosphate buffer | Alternative 1: M199 | Alternative 2: L-Arginine |
|---|---|---|---|---|
| 1 | 1 | 37 | 102 | 99 |
| 2 | 1 | 100 | nd | 87 |
| 3 | 2 | nd | 21 | 90 |
| 4 | 2 | 28 | nd | 83 |
| 5 | 3 | 58 | 76 | 93 |
| 6 | 3 | 87 | nd | 92 |
| 7 | 3 | 100 | nd | 105 |

The addition of L-Arginine to the elution buffer can have a positive effect, which is mainly observed during the SEC for types 1 and 2, while for the IEX it is especially clear for type 2. The addition of alternative 1 (M199) seems to be beneficial as well, however during purification this compound showed to reduce capacity on the IEC, limiting it's usage considerably when compared to alternative 2.

In a further experiment, a high cell density product batch (semi-batch methodology, Thomassen et al., 2014) was produced, infected with Sabin subtype 2 and purified according to Thomassen et al, 2013a and example 1 optimized process, until a 400 times concentrated batch was made (by harvest, filtration and ultrafiltration). This material was aliquoted and stored at −80° C. This material was thawed and purified using size exclusion chromatography with a C16B-resin on an Akta explorer system (GE Healthcare) using different basic amino acid additions at different concentrations to the control 20 mM phosphate buffer. The variations and results are depicted in Table 6 below. The product concentration (D-antigen) is an average of a triplicate [ten Have et al, 2012], the product increase has been calculated and given in a percentage difference.

TABLE 6

Size exclusion chromatography of Sabin subtype 2 using different basic amino acid additions at different concentrations to the control 20 mM phosphate buffer

| | total additive concentration (mM) | D-antigen (product/ml) | % product increase |
|---|---|---|---|
| Control | 0 | 2330 | — |
| L-Arginine | 0.81 | 3065 | 32 |
| | 2.5 | 3273 | 40 |
| | 5 | 3285 | 41 |
| | 25 | 3134 | 35 |
| | 50 | 3200 | 37 |
| | 100 | 2993 | 28 |
| | 150 | 2993 | 28 |
| D-Arginine | 2.5 | 3394 | 46 |
| | 25 | 3101 | 33 |
| L-Lysine | 2.5 | 3226 | 38 |
| | 25 | 2735 | 17 |
| | 150 | 2420 | 4 |
| L-Histidine | 2.5 | 2929 | 26 |
| | 150 | 2386 | 2 |
| D-Histidine | 2.5 | 3577 | 54 |
| | 25 | 3649 | 57 |
| Agmatine | 75 | 3318 | 42 |
| 2.5 mM D-His + 2.5 mM L-Lys | 5 | 3418 | 47 |
| 25 mM D-his + 25 mM L-Lys | 50 | 2735 | 17 |
| 50 mM L-Arg + 50 mM L-His + 50 mM L-Lys | 150 | 3220 | 38 |

From Table 6 it is obvious that different additions and different concentrations have a effect on the recovery of product from the size exclusion chromatography. In all cases the product yield increased from moderate (2%) to high (57%), clearly showing the improvement from the added basic amino acid.

Example 6

Removal of L-Arginine from a Poliovirus Intermediate Purified Product (SEC) Using Diafiltration The addition of a basic amino acid to a virus particle containing solution dissolves and/or prevents aggregate formation. By removing the basic amino acid again, aggregation is expected to return. This was illustrated by producing a poliovirus (Sabin type 2) batch using size exclusion chromatography (Cl6B in a xk26/80 column both GE Healthcare) using an elution buffer containing L-Arginine. The obtained virus product solution was subsequently washed/diafiltrated, as known in the art, using a 100 kD hollow fiber, against a similar buffer solution without the additive at the same rate in which filtrate is removed, thus maintaining a constant retentate volume. The absorbance, as measure for the amount of aggregates, was measured offline using a spectrophotometer (Biowave DNA, WPA), L-Arginine concentration was measured using a NMR. Pressure and conductivity were followed inline with Pendotech disposable sensors.

One diafiltration volume corresponds to the total virus product volume (75 ml) present in the system. The system was left to run for 10 diafiltration volumes with constant flux and TMP (total time 2.5 hours) and samples were taken (and corrected for volume) after each diafiltration volume exchange for analysis.

Figure 4:
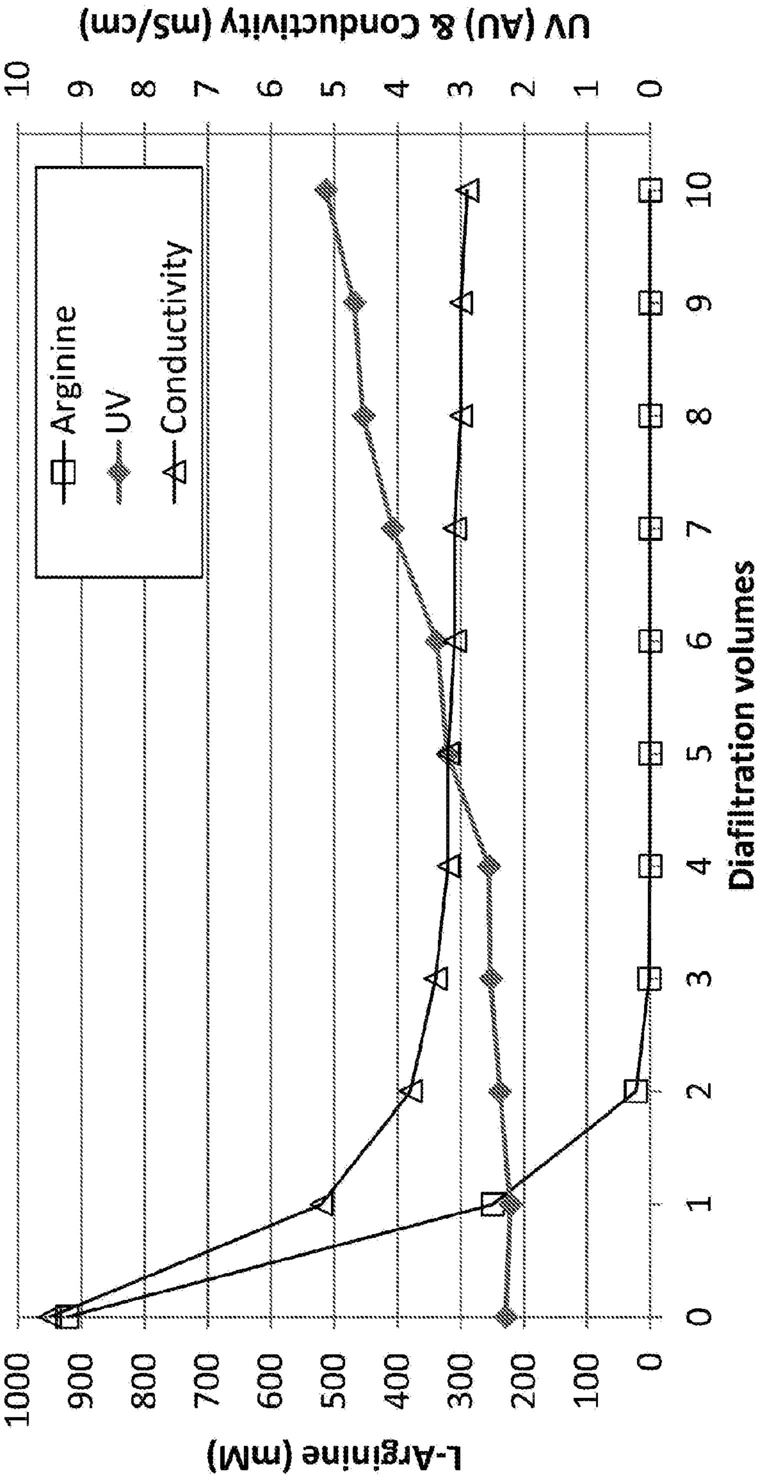
FIG. 4: Removal of L-arginine from a poliovirus (Sabin type 2) SEC product by diafiltration. Removal of L-arginine from a poliovirus (Sabin type 2) SEC product by diafiltration triggers aggregation of virus. An amount of L-arginine (squares) is removed by diafiltration, after ten volumes all L-arginine was removed. Aggregated virus (diamonds) was measured using absorbance measurements. After complete removal of the L-Arginine, poliovirus aggregates are formed in a time dependent manner. Thus removal of L-arginine, as followed by measurements and conductivity change, results in increased light scattering (UV increase) caused by formation of viral aggregates.

Results are depicted in FIG. 4 and show that the L-Arginine concentration quickly drops below the detection limit (1 mM) of the used NMR after 3-4 diafiltration volumes. Corresponding with this decreased concentration of L-Arginine the absorbance increased, indicating aggregation of virus particles. The L-Arginine can be indirectly followed by the conductivity as well. Conductivity drops quickly in parallel with the removal of L-Arginine to reach a final conductivity of 2.9 mS/cm corresponding to the control buffer, indicating that the additive has been removed. The absorbance has more than doubled after 10 diafiltration volumes compared to the starting value when this conductivity value has been reached. This clearly shows that the addition of the basic amino acid was the cause for the reduction in aggregation (as visualized by UV) and that the process is reversible, ie the additive may be removed, albeit aggregation will return.

Example 7

Purification of Wild Type Poliovirus in the Presence or Absence of Basic Amino Acids Wild type polio virus type 2 was produced and purified up to the chromatographic steps in a procedure as described by Thomassen et al (2013a). The material was purified using two different SEC columns, in 40 mM phosphate (pH7.0+/−0.2) buffer. One buffer contained the additive (150 mM L-Arginine) and one buffer was without additive. Both obtained products were subsequently purified on an IEX (DEAF Sepharose Fast Flow, GE Healthcare), again using the two afore mentioned buffers. Table 7 shows the results for the IEX. It is clear that the presence of the additive resulted in a higher product yield by nearly doubling the product yield as measured by ELISA (Ten Have R et al, 2012) and peak area. In both cases, the purification resulted in good purity virus products (based on UV ratio's as determined by Koch and Koch 1985, data not shown).

TABLE 7

SEC and IEX purification of wild type poliovirus in the presence or absence of 150 mM L-Arginine. The peak area corresponds with poliovirus amounts. The measured D-antigen corresponds with immunogenic virus.

| | Without 150 mM L-arginine | With 150 mM L-arginine |
|---|---|---|
| Peak area (mAU*ml) | 3621 | 6006 |
| Poliovirus D-antigen ( DU/ml) | 994 | 1845 |

In a further experiment wild type polio virus type 3 was again produced and purified up to the chromatographic steps in a procedure as described by Thomassen et al (2013a). The material was purified using one SEC column in the regular 40 mM phosphate buffer pH 7.0+/−0.2). The obtained product was split in 2 equal amount portions. To one portion, a highly concentrated buffer containing L-Arginine was added to make a final concentration of 149 mM, while to the other portion the same amount of regular buffer was added to compensate for the diluting effect.

Both products were subsequently purified on a IEX (DEAE Sepharose Fast Flow, GE Healthcare), using the 40 mM phosphate buffer, either with or without additive (150 mM L-Arginine), dependent on the portion to be purified. In Table 8 shows the results for the IEX. It is clear again that the additive resulted in a product yield (based on peak area). In both cases, the purification resulted in good purity virus products (based on UV ratio's as determined by Koch and Koch 1985, data not shown).

TABLE 8

IEX purification of wild typepoliovirus type 3 in the presence or absence of 150 mM L-arginine

| | Without 150 mM L-Arginine | With 150 mM L-Arginine |
|---|---|---|
| Product Peak area (mAU*ml) | 3887 | 4789 |

From Example 7 it is clear that the addition can be made in different ways to be effective, either directly and coeluting or afterwards as a highly concentrated stock compound did not matter. The product containing the additive, in all cases, showed a higher yield. Different forms of additions, such as a solid, through diafiltration or as highly concentrated stock will all result in higher yields as well.

Example 8

Purification of a Chimeric Poliovirus in the Presence or Absence of Basic Amino Acids An experimental poliovirus was obtained, representing a combination/chimera/hybrid of both the wild type virus (bases of Salk-developed IPV) and attenuated virus (Sabin strains). This virus was furthermore crippled by genetic modification to make it less biologically active in mammals to further prevent any severe illness/reversals.

This experimental virus was produced using the existing production process (Bakker et al, 2011 and Thomassen et al, 2013a) on laboratory scale to evaluate its potential. For the chromatographic separation part, both plain 20 mM phosphate buffer (control) and a 20 mM phosphate buffer containing 150 mM L-Arginine were used. The results are depicted in Table 9, which shows the yield of individual unit operations (%) and the combined chromatographic unit operation. Table 9 clearly shows the beneficial effects of the L-Arginine additive as higher overall recoveries are reached.

TABLE 9

| Chimeric poliovirus yield (%) for individual unit operations (SEC and IEX) and combined unit operations | Yield (%) | | | |
|---|---|---|---|---|
| | type 1 | | type 2 | |
| | Control | Additive | Control | additive |
| SEC | 67 | 90 | 60 | 100 |
| IEX | 75 | 88 | 59 | 70 |
| Combined SEC & IEX | 50 | 79 | 35 | 70 |

Example 9

Mixed-Mode/Multimodal Chromatography in the Presence of Basic Amino Acids

The use of an additive in the elution buffer, opens the way for new purification options, such as the use of mixed-mode/multimodal chromatographic separations, instead of regular ion exchange. Hereby both electrostatic and hydrophobic effects are in play to allow bi-dimensional separation of particles, even allowing closely related particles, with regard to isoelectric point, to be separated.

An example is given in Table 10. An HEA Hypercell aliphatic chromatographic resin (Pall Corporation) is used to purify Sabin type 2. Purity of the product is determined on the basis of UV 260/280 ratio in accordance with Koch and Koch (1985), whereby the target ratio for pure poliovirus is in the range of 1.60-1.80. Without L-Arginine present the HEA-purified virus has an UV 260/280 ratio of 0.98, whereas virus purified on the HEA column in the presence of 150 mM L-Arginine suddenly reaches a high purity as indicated by an UV 260/280 ratio of 1.76, i.e. within the target range.

TABLE 10

| Purity of viral polio product on a multimodal chromatographic resin | target | control | additive |
|---|---|---|---|
| UV260/280 ratio | 1.60-1.80 | 0.98 | 1.76 |

The use of new and more modern resins creates new options for viral purification.

Example 10

Effects of Different Basic Amino Acid and Derivatives Thereof on Reducing of Aggregation of Poliovirus A black 96-wells plate, chimney shaped with a clear bottom, was used for screening different compounds and concentrations against an aggregated intermediately purified batch of polio (Sabin, type 1, derived from a size exclusion chromatography step in a plain phosphate buffer).

Stock solutions of the various compounds were prepared in a 96-deep wells plate by mixing concentrated stock solutions with buffer (both pH 7.0+/−0.2) to a pre-determined molarity, after which these were added to the black 96 well plate in equal amounts with the virus preparation to be tested (1:1).

Figure 5:
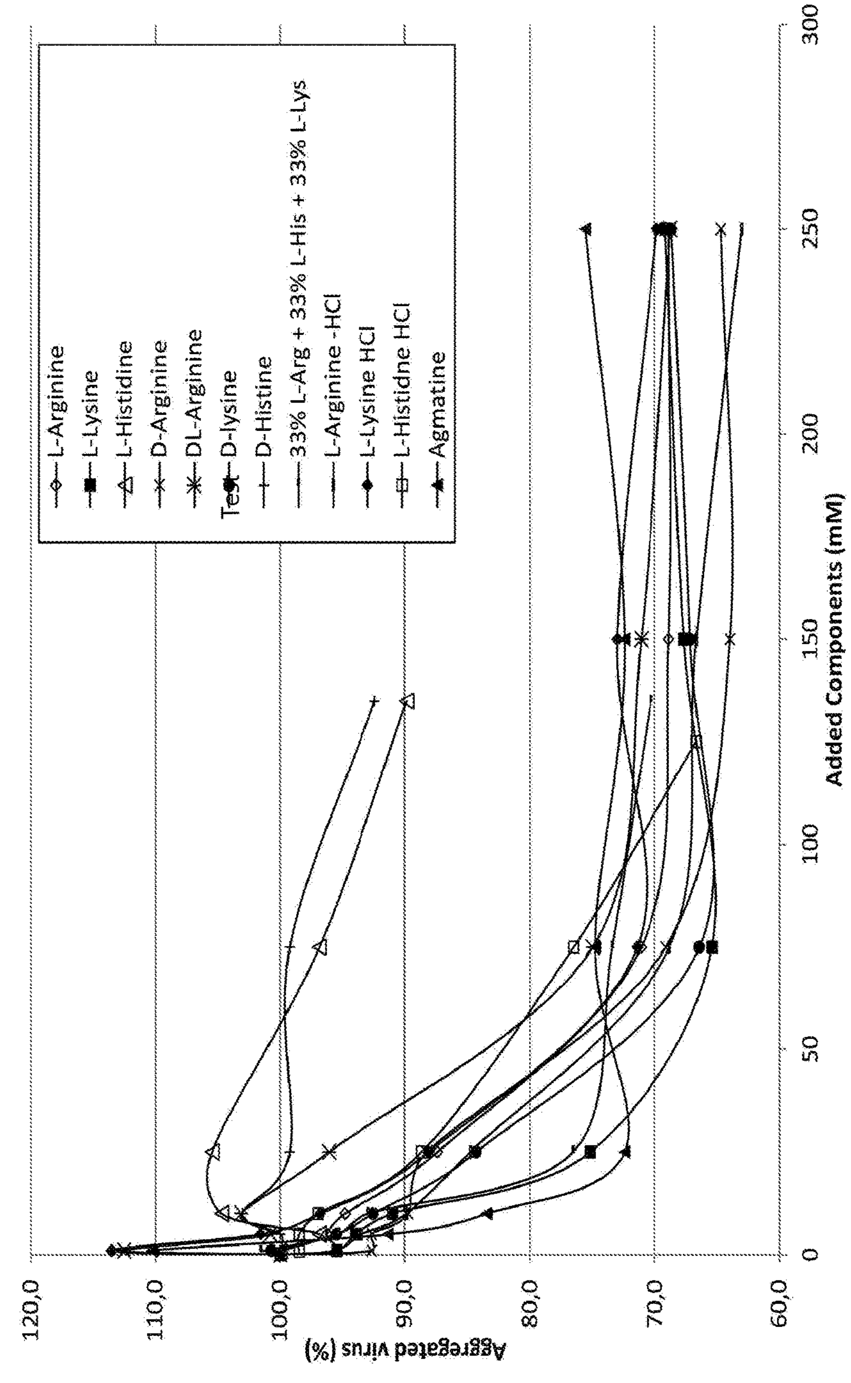
FIG. 5: Effects of different basic amino acid and derivatives thereof on the reduction of poliovirus aggregates. The different compounds clearly show an effect, dependent on their type and concentration. For instance agmatine, L-lysine and the mixture of 3 basic amino acids the reduction most profound in the lower concentration range upto 50 mM. In all cases a reduction of aggregates from the starting material, as measured by UV, is clearly visible and dependent on their concentration.

The resulting plate was mixed on a shaker platform and absorbance (590 nm) was measured after 5 minutes. The results are depicted in FIG. 5.

REFERENCES

Albrecht P., Van Steenis G., Van Wezel A L., Salk J. Standardization of poliovirus neutralizing antibody tests. Rev Infect Dis, 6 (May-June (Suppl. 2)) (1984), pp. S540-S544.

Aylward B, Tangermann R. The global polio eradication initiative: Lessons learned and prospects for success. Vaccine 29(S4), D80-D85 (2011).

Arakawa, T., John S Philo, Kouhei Tsumoto, Ryosuke Yumioka, Daisuke Ejima. Elution of antibodies from a Protein-A column by aqueous arginine solutions. Protein Expression and Purification. 2004 volume 36 (issue 2) Pages 244-248.

Arakawa, T.; Kita, Y.; Koyama, A. H. Synergistic virus inactivation effects of arginine. Biotechnol. J. 2009, 4, 174-178.

Bakker W A, Thomassen Y E, van't Oever A G, Westdijk J, van Oijen M G, Sundermann L C, van't Veld P, Sleeman E, van Nimwegen F W, Hamidi A, Kersten G F, van den Heuvel N, Hendriks J T, van der Pol L A. Vaccine. 2011 Sep. 22; 29(41):7188-96.

Baynes B M, Trout B L. Rational design of solution additives for the prevention of protein aggregation. Biophys J. 2004 September; 87(3):1631-9.

Baynes B M, Wang D I, Trout B L. Role of arginine in the stabilization of proteins against aggregation. Biochemistry. 2005 Mar. 29; 44(12):4919-25.

Chumakov K, Ehrenfeld E, Wimmer E, Vadim I. Vaccination against polio should not be stopped. Nature Rev. Microbiol. 5, 952-958 (2007).

Chumakov K, Ehrenfeld E, Plotkin S. New generation of inactivated poliovirus vaccines for universal immunization after eradication of poliomyelitis. Clin. Infect. Dis. 47(12), 1587-1592 (2008).

Cromwell M E M, Hilario E, Jacobson F. Protein aggregation and bioprocessing. The American Association of Pharmaceutical Scientists. 2006 September; 8(3): E572-E579.

Das T K. Protein particulate detection issues in biotherapeutics development—current status. AAPS PharmSciTech. 2012 June; 13(2):732-46.

Desnues, C., and D. Raoult. 2010. Inside the lifestyle of the virophage. Intervirology 53:293-303.

Duchene M, Peetermans, d'Hondt E, Harford N, Fabry L, Stephenne J. Production of poliovirus vaccines: past, present, and future. Viral Immunology 3(4), 243-272 (1990).

Nathanson N, Kew O M. From Emergence to Eradication: The Epidemiology of Poliomyelitis Deconstructed. Am. J. Epidemiol. (2010) 172(11): 1213-1229.

Fields Virology, $5^{th}$ edition, 2007; Bernard N. Fields, David Mahan Knipe, Peter M. Howley, Wolters Kluwer.

Gu Z et al. Inhibition of aggregation by media selection, sample loading and elution in size exclusion chromatographic refolding of denatured bovine carbonic anhydrase B.J. Biochem Biophys Methods. 2003. 56(1-3):165-75).

Hamidi A, Bakker W A M. Innovative IPV from attenuated Sabin poliovirus or newly designed alternative seed strains. Pharmaceutical Patent Analyst (2012) 5(1):589-599.

Heinsbroek E, Ruitenberg E J. The global introduction of inactivated polio vaccine can circumvent the oral polio vaccine paradox. Vaccine 28(22), 3778-3783 (2010).

Heymann D L, Sutter R W, Aylward R B, A vision of a world without polio: The OPV cessation strategy. Biologicals 34(2), 75-79 (2006).

Heymann D L, Sutter R W, Aylward R B. A global call for new polio vaccines. Nature 434, 699-700 (2005).

Holmes E C. Viral evolution in the genomic age. PLoS Biol. 2007; 5(10):e278.

Jonges M, Liu W M, van der Vries E, Jacobi R, Pronk I, Boog C, Koopmans M, Meijer A, Soethout E. Influenza virus inactivation for studies of antigenicity and phenotypic neuraminidase inhibitor resistance profiling. 2010, J. Clin. Microbiol. 48:928-940.

Koonin E V, Senkevich T G, Dolja V V. The ancient Virus World and evolution of cells. Biol Direct. 2006 Sep. 19; 1:29.

Kew O M, Sutter R W, de Gourville E M, Dowdle W R, Pallansch M A. Vaccine-derived polioviruses and the endgame strategy for global polio eradication. Ann. Rev. Microbiol. 59, 587-635 (2005).

Koch and Koch. The molecular biology of poliovirus. 1985 Springer-Verlag Wien-New York ISBN 3-211-81763-8.

Li Y, Weiss W F, Roberts C J. Characterization of high-molecular-weight non native aggregates and aggregation kinetics by size exclusion chromatography with inline multi-angle laser light scattering. Journal of pharmaceutical sciences 2009 vol 98 issue 11 p 3997-4016.

Lee Sang-Won, Philip F. Markham, Mauricio J. C. Coppo, Alistair R. Legione, John F. Markham, Amir H. Noormohammadi, Glenn F. Browning, Nino Ficorilli, Carol A. Hartley, Joanne M. Devlin. Attenuated Vaccines Can Recombine to Form Virulent Field Viruses. Science 13 Jul. 2012: 188.

Montagnon B J, Fanget B, Vincent-Falquet J C. Industrial-scale production of inactivated poliovirus vaccine prepared by culture of Vero cells on microcarrier. Rev Infect Dis. 1984 May-June; 6 Suppl 2:S341-4.

Montagnon B, Vincent-Falquet J C, Fanget B. Thousand liter scale microcarrier culture of Vero cells for killed polio virus vaccine. Promising results. Dev Biol Stand. 1983; 55:37-42.

Morgan, J. F. and Campbell, M. E. (1955) J. Natl. Cancer Inst., 16:557.

Morgan, J. F., Morton, H. J. and Parker R. C. (1950) Proc. Soc. Exp. Biol. Med., 73:1.

Nathanson & Kew. From emergence to eradication: the epidemiology of poliomyelitis deconstructed. Am J Epidemiol. 2010 Dec. 1; 172(11):1213-29.

Pearson, H. 2008. 'Virophage' suggests viruses are alive. Nature 454:677.

Robinson H L. Viral attenuation by design. Nature Biotechnology. 2008 September; 26(9):1000-1.

Sanders P, Edo-Matas D, Custers J H H V, Koldijk M R, Klaren V, Turk M, Luitjens A, Bakker W A M, Uytdehaag F, Goudsmit J, Lewis J A, Schuitemaker H, PER.C6® cells as a serum-free suspension cell platform for the production of high titer poliovirus: A potential low cost of goods option for world supply of inactivated poliovirus vaccine. Vaccine. 2013 Jan. 21; 31(5):850-6.

Sun L, Young L N, Zhang X, Boudko S P, Fokine A, Zbornik E, Roznowski A P, Molineux I J, Rossmann M G, Fane B A. Icosahedral bacteriophage ΦX174 forms a tail for DNA transport during infection. Nature. 2014 Jan. 16; 505(7483):432-5.

Taylor, J. P.; Hardy, J.; Fischbeck; K. H. Toxic proteins in neurodegenerative disease. Science. 2002 Jun. 14; 296 (5575):1991-5.

Taylor D J, Ballinger M J, Bowman S M, Bruenn J. Virus-host co-evolution under a modified nuclear genetic code. Peed 2013 Mar. 5; 1e50.

Ten Have R, Thomassen Y E, Hamzink M R, Bakker W A, Nijst O E, Kersten G, Zomer G. Development of a fast ELISA for quantifying polio D-antigen in in-process samples. Biologicals. 2012 January; 40(1):84-7.

Thomassen Y E, van Sprang E N, van der Pol L A, Bakker W A. Multivariate data analysis on historical IPV production data for better process understanding and future improvements. Biotechnology & Bioengineering 2010 Sep. 1; 107 (1):96-104.

Thomassen Y E, Rubingh O, Wijffels R H, van der Pol L A, Bakker W A, Vaccine. 2014 May 19; 32(24):2782-8. doi: 10.1016/j.vaccine.2014.02.022. Epub 2014 Feb. 26.

Thomassen Y E, van't Oever A G, Vinke M, Spiekstra A, Wijffels R H, van der Pol L A, Bakker W A. Scale-down of the inactivated polio vaccine production process. Biotechnol Bioeng. 2013a May; 110(5):1354-65.

Thomassen, Y E, van't Oever, A G, van Oijen M G C T, Wijffels, R. H., van der Pol, L A, Bakker, W A M. Next generation inactivated polio vaccine manufacturing to support post polio-eradication biosafety goals. PLOS One. 2013b Dec. 12; 8(12):e83374Thompson K M, Tebbens R J. Current polio global eradication and control policy options: perspectives from modeling and prerequisites for oral poliovirus vaccine cessation. Expert Review of Vaccines 11(4), 449-459 (2012).

Utsunimoya, H.; Ichinose, M.; Tsujimoto, K.; Katsuyama, Y.; Yamasaki, H.; Koyama, A. H.; Ejima, D.; Arakawa, T. Co-operative thermal inactivation of herpes simplex virus and influenza virus by arginine ans NaCl. Int. J. Pharm. 2009, 366, 99-102.

Van Wezel A L, van Steenis G, Hannik C A, Cohen H. 1978. New approach to the production of concentrated and purified inactivated polio and rabies tissue culture vaccines. Develop, biol. Standard. 41: 159-168.

Verdijk P, Rots N Y, Bakker W A M. Clinical development of a novel inactivated poliomyelitis vaccine based on attenuated Sabin poliovirus strains. Expert Review of Vaccines (2011) 10(5):635-644.

Wei Wang. Protein aggregation and its inhibition in biopharmaceuticals. International journal of pharmaceuticles 2005; 289: 1-30.

Westdijk, J., et al., Characterization and standardization of Sabin based inactivated polio vaccine: proposal for a new antigen unit for inactivated polio vaccines. Vaccine, 2011. 29(18): p. 3390-7.

Widjojoatmodjo M N, Boes J, van Bers M, van Remmerden Y, Roholl P J, Luytjes W. A highly attenuated recombinant human respiratory syncytial virus lacking the G protein induces long-lasting protection in cotton rats. Virol J. 2010 Jun. 2; 7:114.

Yamasaki, H.; Tsujimoto, K.; Koyama, A. H.; Ejima, D.; Arakawa, T. Arginine facilitates inactivation of enveloped viruses. J. Pharm. Sci. 2008, 97, 3063-3073.

Zor and Selinger, Linearization of the Bradford protein assay increases its sensitivity: theoretical and experimental studies. Anal Biochem. 1996 May 1; 236(2):302-8.

ABBREVIATIONS

AU—Absorbance units
CCID50—50% cell culture infectious dose
CFF—Cross Flow Filtration
cm—centimeter
CPE—Cytopathological Effect DEAE—Diethylaminoethanol
DF—Diafiltration
DLS—Dynamic Light Scattering
DNA—Deoxyribonucleic acid
DO—Dissolved Oxygen
DSP—Down Stream Processing
DU—D-antigen Unit
EID50—50% egg infectious dose
ELISA—Enzyme-linked immuno sorbent assay
E-MEM—Eagle's minimal essential medium
FTU—Formazin Turbidity Unit
HCP—Host Cell Protein
HEA—hexylamine
HPV—Human papillomavirus
HVAC—Heating, Ventilation, and Air Conditioning
IEC/IEX—Ion Exchange Chromatography
IPV—inactivated polio Vaccine
kD—kiloDalton
M199—Medium 199
MALS—Multi Angle Light Scattering
MKC—Monkey kidney cell
mM—milliMolar
MOI—multiplicity of infection
mS—milli-Siemens
NIBSC—National Institute for Biological Standards and Control
nm—nanometer
NMR—nuclear magnetic resonance
NTU—Nephelometric Turbidity Unit
OD—Optical Density
OPV—Oral Polio Vaccine
PBS—Phosphate Buffered Saline
RIVM—National Institute for Public Health and Environment
RNA—Ribonucleic Acid
RSV—Respiratory Syncytial Virus
SEC—Size exclusion Chromatography
sIPV—Sabin-based inactivated Polio Vaccine
SPF—Specific pathogen Free
SRID—Single Radial Immunodiffusion
TCID50—50% Tissue Culture Infective Dose
TFF—Tangential Flow Filtration
UF—Ultra Filtration
USP—Upstream processing
UV—Ultra Violet
VAPP—Vaccine Associated Paralytic Poliomyelitis
VDPV—Vaccine Derived Poliovirus
VLP—Virus Like Particle

The invention claimed is:

1. A method for producing a composition comprising Enteroviral particles, the method comprising, sequentially:

(a) purifying Enteroviral particles from a medium containing Enteroviral particles, whereby during at least a part of the purification a basic amino acid or a derivative thereof is present at a concentration between 0.5-1000 mM to prevent or reduce aggregation of the Enteroviral particles; and, optionally, at least one of:

(b) inactivating the Enteroviral particles; and, (c) formulating the Enteroviral particles, wherein the basic amino acid or derivative thereof is selected from the group consisting of arginine, lysine, histidine, arginine-HCl , lysine-HCl , histidine-HCl , agmatine, L-arginine ethyl ester dihydrochloride, tranexamic acid, DL-5-hydroxylysine hydrochloride, L-lysine methyl ester dihydrochloride, 3-methyl-L-histidine, salts thereof and combinations thereof.

2. The method according to claim 1, wherein the basic amino acid or derivative thereof is present at a concentration sufficient to prevent or reduce aggregation of the Enteroviral particles during at least a part of step (b), and wherein, optionally, also during step (c) the basic amino acid or derivative thereof is present at a concentration sufficient to prevent or reduce aggregation of the Enteroviral particles to formulate a pharmaceutical composition comprising the Enteroviral particles and optionally a concentration of the basic amino acid or derivative thereof sufficient to prevent or reduce aggregation of the Enteroviral particles.

3. The method according to claim 1, wherein the concentration of the basic amino acid or derivative thereof that is sufficient to prevent or reduce aggregation of the Enteroviral particles is maintained throughout the entire duration of at least one of steps (a), (b) and (c).

4. The method according to claim 1, wherein the concentration of the basic amino acid or derivative thereof is a concentration of at least 0.81 mM.

5. The method according to claim 4, wherein the concentration of the basic amino acid or derivative thereof is a concentration between 0.81-500 mM.

6. The method according to claim 1, wherein the Enteroviral particles are virus-like particles of an *Enterovirus*.

7. The method according to claim 1, wherein the Enteroviral particles are of an *Enterovirus* selected from the group consisting of polioviruses, Coxsackie A viruses, Coxsackie B viruses, Echoviruses, Rhinoviruses and Enteroviruses 68, 69, 70, 71 and 73.

8. The method according to claim 7, wherein the Enteroviral particles comprise polioviruses of the serotypes 1, 2 and 3.

9. The method according to claim 8, wherein the composition comprising Enteroviral particles is a vaccine.

10. The method according to claim 9, wherein the vaccine is an Inactivated Polio Vaccine (IPV).

11. A method of preventing or reducing aggregation of Enteroviral particles during purification of the Enteroviral particles from a medium, the method comprising adding to a composition comprising Enteroviral particles a basic amino acid or derivative thereof selected from the group consisting of arginine, lysine, histidine, arginine-HCl , lysine-HCl , histidine-HCl , agmatine, L-arginine ethyl ester dihydrochloride, tranexamic acid, DL-5-hydroxylysine hydrochloride, L-lysine methyl ester dihydrochloride, 3-methyl-L-histidine, salts thereof and combinations thereof, wherein during at least a part of the purification the basic amino acid or a derivative thereof is present at a concentration between 0.5-1000 mM to prevent or reduce aggregation of the viral component.

12. The method according to claim 11, wherein the Enteroviral particles are of an *Enterovirus* selected from the group consisting of polioviruses, Coxsackie A viruses, Coxsackie B viruses, Echoviruses, Rhinoviruses and Enteroviruses 68, 69, 70, 71 and 73.

13. The method according to claim 11, wherein the Enteroviral particles comprise polioviruses of the serotypes 1, 2 and 3.

14. The method according to claim 11, wherein the Enteroviral particles are an Inactivated Polio Vaccine (IPV).

* * * * *